(12) United States Patent
Hay

(10) Patent No.: US 10,459,615 B2
(45) Date of Patent: *Oct. 29, 2019

(54) APPARATUS AND METHOD FOR ANALYZING PERIODIC MOTIONS IN MACHINERY

(71) Applicant: RDI TECHNOLOGIES, INC., Knoxville, TN (US)

(72) Inventor: Jeffrey R. Hay, Louisville, KY (US)

(73) Assignee: RDI TECHNOLOGIES, INC., Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/757,245

(22) Filed: Dec. 9, 2015

(65) Prior Publication Data

US 2016/0217587 A1 Jul. 28, 2016

Related U.S. Application Data

(60) Provisional application No. 62/090,729, filed on Dec. 11, 2014, provisional application No. 62/139,127, (Continued)

(51) Int. Cl.
*G06K 9/00* (2006.01)
*G06F 3/0484* (2013.01)
(Continued)

(52) U.S. Cl.
CPC ........ *G06F 3/04847* (2013.01); *A61B 5/0077* (2013.01); *A61B 5/01* (2013.01); *A61B 5/024* (2013.01); *A61B 5/0816* (2013.01); *A61B 5/165* (2013.01); *A61B 5/4815* (2013.01); *A61B 5/7435* (2013.01); *G01N 29/44* (2013.01); *G06F 16/7335* (2019.01); *G06K 9/00335* (2013.01);
(Continued)

(58) Field of Classification Search
None
See application file for complete search history.

(56) References Cited

U.S. PATENT DOCUMENTS 5,517,251 A 5/1996 Rector et al.
5,666,157 A 9/1997 Aviv
(Continued)

OTHER PUBLICATIONS

Wadhwa et al., "Phase-based Video Motion Processing", also see YouTube https://www.youtube.com/watch?v=W7ZQ-FG7Nvw, SIGGRAPH 2013.*

(Continued)

*Primary Examiner* — Randolph I Chu
(74) *Attorney, Agent, or Firm* — Wyatt, Tarrant & Combs, LLP; Stephen C. Hall

(57) ABSTRACT

An apparatus for monitoring machine components includes:
a device for acquiring video image files;
a data analysis system including processor and memory;
a computer program operating in said processor to identify an area in said images where periodic movements associated with a mechanical vibration may be detected and quantified using an adaptive array comparison procedure; and,
an interface to output said vibration information in a usable form.

The apparatus may further include a graphical user interface and an accessible database. An associated method for using the apparatus is also disclosed.

10 Claims, 23 Drawing Sheets

Related U.S. Application Data filed on Mar. 27, 2015, provisional application No. 62/141,940, filed on Apr. 2, 2015, provisional application No. 62/139,110, filed on Apr. 14, 2015, provisional application No. 62/146,744, filed on Apr. 13, 2015, provisional application No. 62/154,011, filed on Apr. 28, 2015, provisional application No. 62/161,228, filed on May 13, 2015, provisional application No. 62/209,979, filed on Aug. 26, 2015.

(51) Int. Cl.

| | | |
|---|---|---|
| *G06F 16/732* | (2019.01) | |
| *A61B 5/00* | (2006.01) | |
| *A61B 5/01* | (2006.01) | |
| *A61B 5/024* | (2006.01) | |
| *A61B 5/08* | (2006.01) | |
| *A61B 5/16* | (2006.01) | |
| *G06T 7/00* | (2017.01) | |
| *G01N 29/44* | (2006.01) | |
| *G06T 7/11* | (2017.01) | |
| *G06T 7/246* | (2017.01) | |
| *G06T 7/262* | (2017.01) | |
| *H04N 7/18* | (2006.01) | |

(52) U.S. Cl.
CPC ........ *G06K 9/00771* (2013.01); *G06T 7/0016* (2013.01); *G06T 7/11* (2017.01); *G06T 7/248* (2017.01); *G06T 7/262* (2017.01); *G01N 2291/028* (2013.01); *G06T 2200/24* (2013.01); *G06T 2207/10016* (2013.01); *G06T 2207/20056* (2013.01); *G06T 2207/20216* (2013.01); *G06T 2207/30004* (2013.01); *G06T 2207/30164* (2013.01); *H04N 7/18* (2013.01)

(56) References Cited

U.S. PATENT DOCUMENTS

| | | | |
|---|---|---|---|
| 6,028,626 A | 2/2000 | Aviv | |
| 6,295,383 B1 | 9/2001 | Smitt et al. | |
| 6,422,741 B2 | 7/2002 | Murphy et al. | |
| 6,727,725 B2 | 4/2004 | Devaney et al. | |
| 6,774,601 B2 | 4/2004 | Swartz et al. | |
| 6,792,811 B2 | 9/2004 | Argento et al. | |
| 7,622,715 B2 | 11/2009 | Ignatowicz | |
| 7,672,369 B2 | 3/2010 | Garakani et al. | |
| 7,710,280 B2 | 5/2010 | McLellan | |
| 7,862,188 B2 | 1/2011 | Luty et al. | |
| 7,903,156 B2 | 3/2011 | Nobori et al. | |
| 8,119,986 B1 | 2/2012 | Garvey, III et al. | |
| 8,149,273 B2 | 4/2012 | Liu et al. | |
| 8,170,109 B2 | 5/2012 | Gaude et al. | |
| 8,242,445 B1 | 8/2012 | Scanlon et al. | |
| 8,351,571 B2 | 1/2013 | Brinks et al. | |
| 8,374,498 B2 | 2/2013 | Pastore | |
| 8,475,390 B2 | 7/2013 | Heaton et al. | |
| 8,483,456 B2 | 7/2013 | Nagatsuka et al. | |
| 8,502,821 B2 | 8/2013 | Medina et al. | |
| 8,515,711 B2 | 8/2013 | Mitchell et al. | |
| 8,526,674 B2 | 9/2013 | Patti | |
| 8,537,203 B2 | 9/2013 | Seibel et al. | |
| 8,693,735 B2 | 4/2014 | Kielkopf et al. | |
| 8,720,781 B2 | 5/2014 | Wang et al. | |
| 8,731,241 B2 | 5/2014 | Johnson et al. | |
| 8,765,121 B2 | 7/2014 | Maslowski et al. | |
| 8,774,280 B2 | 7/2014 | Tourapis et al. | |
| 8,797,439 B1 | 8/2014 | Coley et al. | |
| 8,803,977 B2 | 8/2014 | Uchima et al. | |
| 8,811,708 B2 | 8/2014 | Fischer et al. | |
| 8,823,813 B2 | 9/2014 | Manzel et al. | |
| 8,831,370 B2 | 9/2014 | Archer | |
| 8,874,374 B2 | 10/2014 | Bogucki | |
| 8,879,789 B1 | 11/2014 | Figov et al. | |
| 8,879,894 B2 | 11/2014 | Neuman et al. | |
| 8,884,741 B2 | 11/2014 | Cavallaro et al. | |
| 8,897,491 B2 | 11/2014 | Ambrus et al. | |
| 8,924,163 B2 | 12/2014 | Hudson et al. | |
| 9,006,617 B2 | 4/2015 | Mullen | |
| 9,075,136 B1 | 7/2015 | Joao | |
| 9,805,475 B2 | 10/2017 | Rubinstein et al. | |
| 2004/0032924 A1 | 2/2004 | Judge, Jr. | |
| 2004/0081369 A1 | 4/2004 | Gindele et al. | |
| 2004/0160336 A1 | 8/2004 | Hoch et al. | |
| 2004/0184529 A1 | 9/2004 | Henocq et al. | |
| 2006/0009700 A1 | 1/2006 | Brumfield et al. | |
| 2006/0049707 A1 | 3/2006 | Vuyyuru | |
| 2007/0061043 A1 | 3/2007 | Ermakov et al. | |
| 2007/0276270 A1 | 11/2007 | Tran | |
| 2009/0010570 A1 | 1/2009 | Yamada et al. | |
| 2010/0033579 A1 | 2/2010 | Yokohata et al. | |
| 2010/0042000 A1 | 2/2010 | Schuhrke et al. | |
| 2010/0091181 A1 | 4/2010 | Capps | |
| 2010/0328352 A1* | 12/2010 | Shamir ............. G06T 3/0012 345/661 |
| 2011/0019027 A1 | 1/2011 | Fujita et al. | |
| 2011/0152729 A1 | 6/2011 | Oohashi et al. | |
| 2012/0207218 A1 | 8/2012 | Asamura et al. | |
| 2013/0060571 A1 | 3/2013 | Soemo et al. | |
| 2013/0176424 A1 | 7/2013 | Weil | |
| 2013/0201316 A1 | 8/2013 | Binder et al. | |
| 2013/0342691 A1 | 12/2013 | Lewis et al. | |
| 2014/0002667 A1 | 1/2014 | Cheben et al. | |
| 2014/0072190 A1* | 3/2014 | Wu ............. G06T 7/262 382/128 |
| 2014/0072228 A1 | 3/2014 | Rubinstein et al. | |
| 2014/0072229 A1* | 3/2014 | Wadhwa ............. G06K 9/481 382/197 |
| 2014/0112537 A1 | 4/2014 | Nister et al. | |
| 2014/0169763 A1 | 6/2014 | Nayak et al. | |
| 2014/0205175 A1 | 7/2014 | Tanaka et al. | |
| 2014/0236036 A1 | 8/2014 | de Haan et al. | |
| 2014/0341470 A1 | 11/2014 | Lee et al. | |
| 2015/0134545 A1 | 5/2015 | Mann et al. | |
| 2015/0221534 A1 | 8/2015 | van der Meulen | |

OTHER PUBLICATIONS

Wu et al., "Eulerian Video Magnification for Revealing Subtle Changes in the World", ACM Transactions on Graphics (TOG)—Proceedings of ACM SIGGRAPH 2012 TOG Homepag, evol. 31 Issue 4, Jul. 2012, Article No. 65.*

Liu et al., "Motion magnification", ACM Transactions on Graphics (TOG)—Proceedings of ACM SIGGRAPH 2005 TOG Homepage, vol. 24 Issue 3, Jul. 2005.*

Rubinstein et al. ("Revealing Invisible Changes in the world (YouTube)", YouTube https://www.youtube.com/watch?v=e9ASH8IBJ2U, 2012.*

Rubinstein et al. ("Eulerian Video Magnification (YouTube)", YouTube https://www.youtube.com/watch?v=ONZcjs1Pjmk, 2012).*

Liu et al., Motion Magnification, SIGGRAPH, 2005.*

Hay, J.R. "High Dynamic Range Imaging for the Detection of Motion", pp. 18-141; dissertation University of Louisville (Kentucky); May 2011.

Mazen, et al.; A vision-based approach for the direct measurement of displacements in vibrating systems; article from Smart Materials and Structures; 2003; 12; pp. 785-794; IOP Publishing LTD; UK.

* cited by examiner

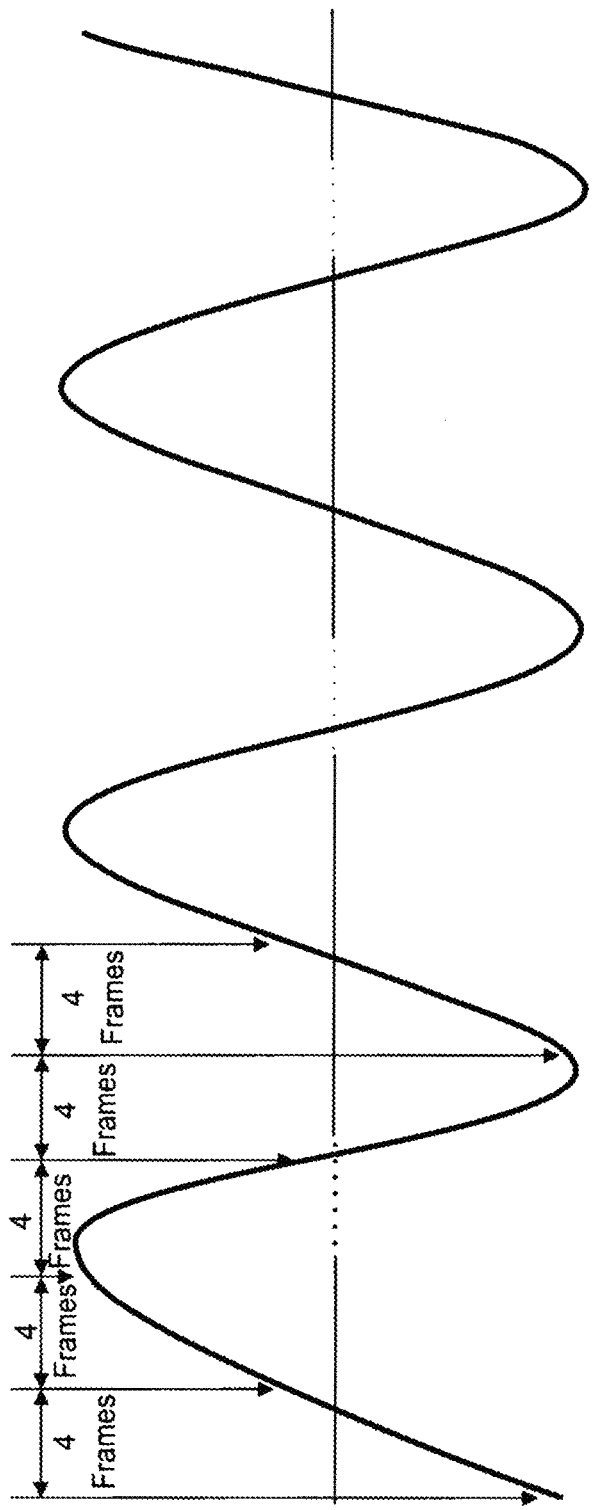

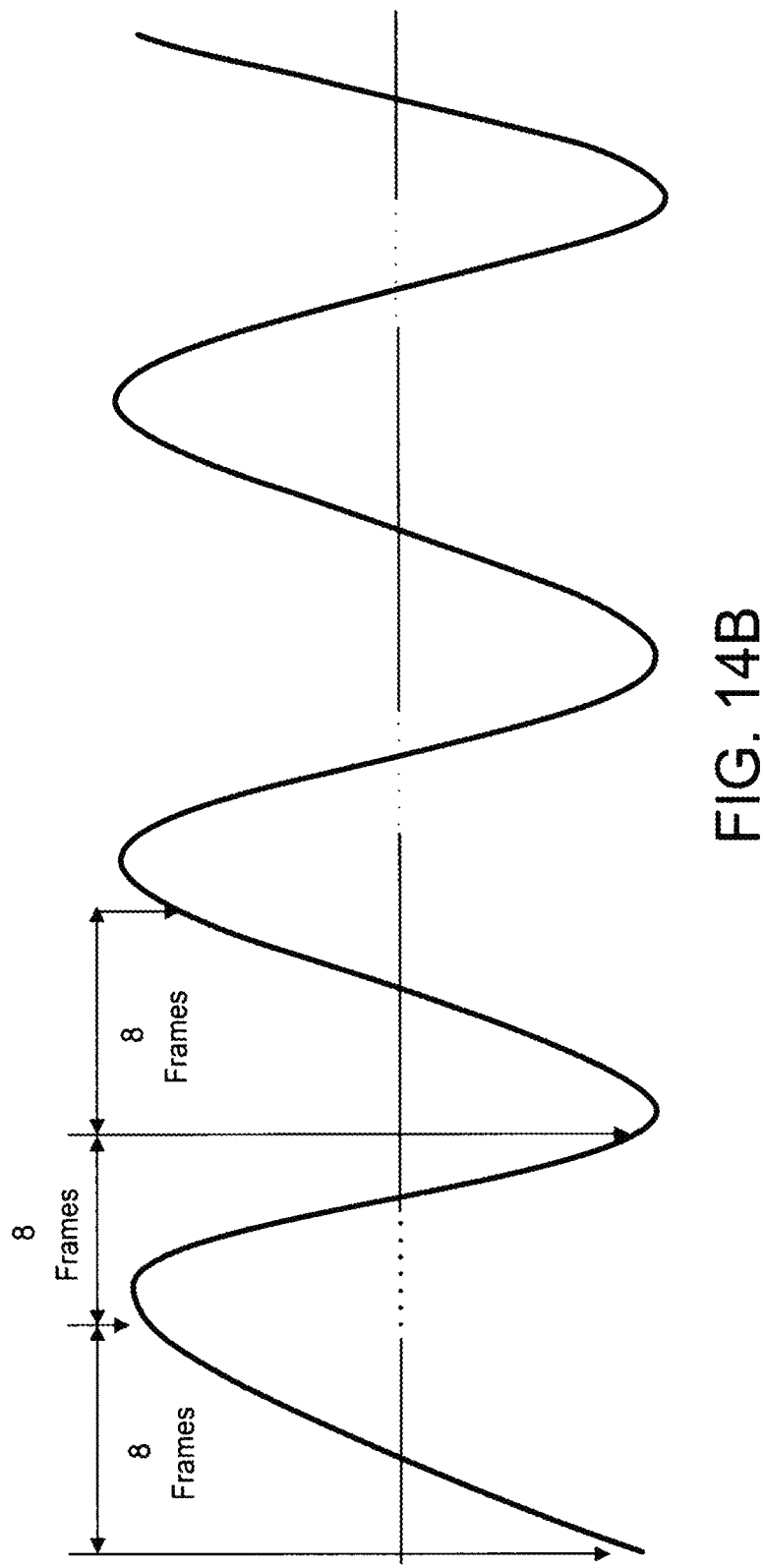

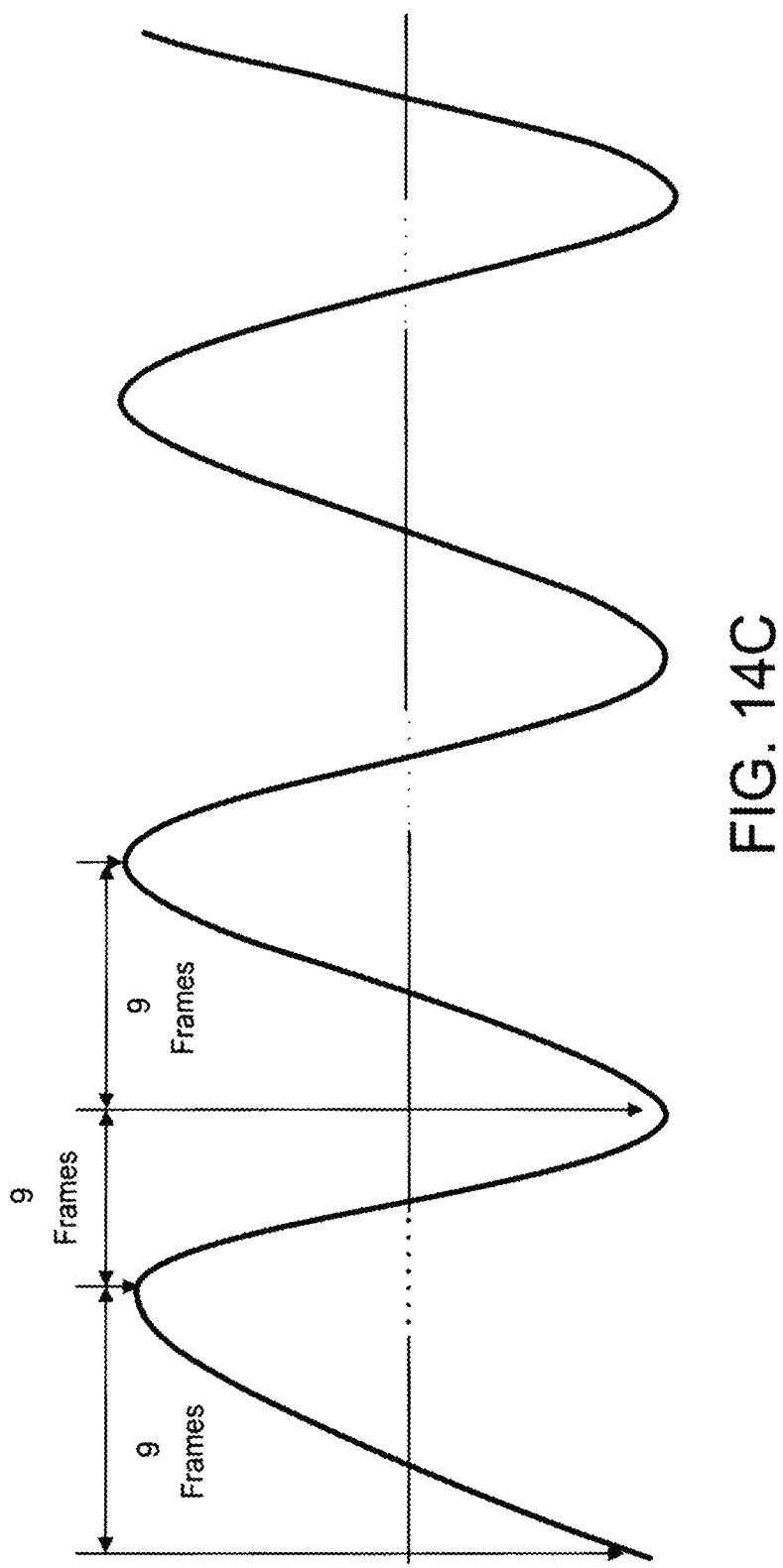

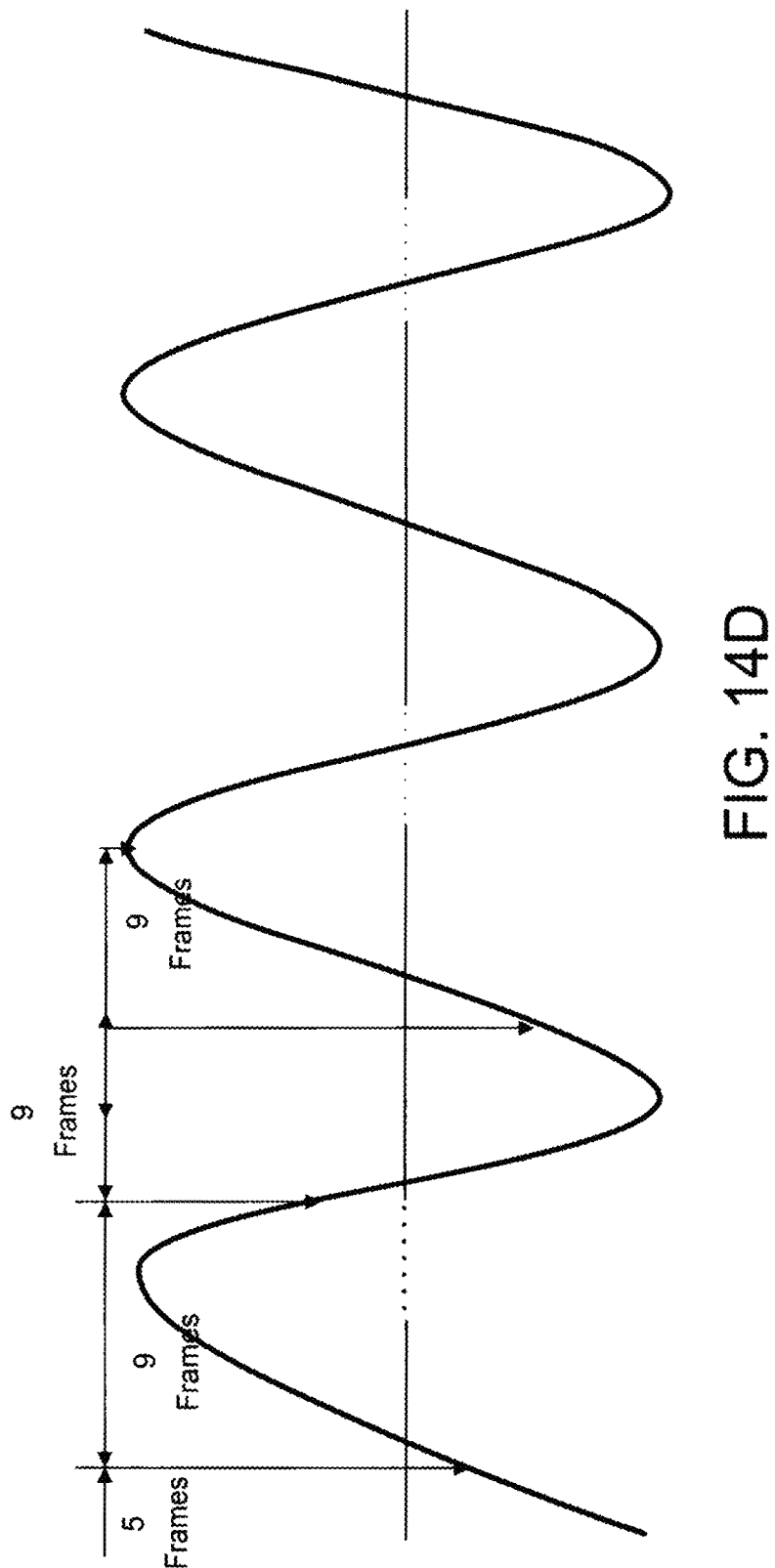

APPARATUS AND METHOD FOR ANALYZING PERIODIC MOTIONS IN MACHINERY

CROSS-REFERENCE TO RELATED APPLICATIONS

This application claims the benefit of each of the following Provisional Patent Applications filed by the present inventors: Ser. No. 62/090,729, "Optical detection of periodic movement", filed on Dec. 11, 2014; Ser. No. 62/139,127, "Method for determining, comparing, measuring, and displaying phase", filed on Mar. 27, 2015; Ser. No. 62/141,940, "Method and system for analysis of structures and objects from spatio-temporal data", filed on Apr. 2, 2015; Ser. No. 62/139,110, "Adaptive array comparison", filed on Apr. 14, 2015; Ser. No. 62/146,744, "Method of analyzing, displaying, organizing, and responding to vital signals", filed on Apr. 13, 2015; Ser. No. 62/154,011, "Non contact optical baby monitor that senses respiration rate and respiratory waveform", filed on Apr. 28, 2015; Ser. No. 62/161,228, "Multiple region perimeter tracking and monitoring", filed on May 13, 2015; and Ser. No. 62/209,979, "Comparative analysis of time-varying and static imagery in a field", filed on Aug. 28, 2015, by the present inventors; the disclosures of each of which are incorporated herein by reference in their entirety.

This application is related to the following applications, filed on Dec. 9, 2015 and having the same inventor: Ser. No. 14/757,256, "Method of analyzing, displaying, organizing, and responding to vital signals", U.S. Publication No. 2016/0210747; Ser. No. 14/757,255, "Non-contacting monitor for bridges and civil structures", U.S. Publication No. 2016/0171309; Ser. No. 14/757,259, "Method of adaptive array comparison for the detection and characterization of periodic motion", U.S. Publication No. 2016/0217588; the entire disclosures of each and every one of which are incorporated herein by reference.

BACKGROUND OF THE INVENTION

Field of the Invention

The invention pertains to apparatus and methods for analyzing periodic movements in machinery. More particularly, the invention pertains to a non-contacting system for analyzing vibrations and other periodic movements in machinery and process equipment for predictive maintenance and other purposes.

Description of Related Art

All machines and moving systems produce vibrations of various kinds, some of which may be characteristic of normal operation and others of which may indicate off-normal conditions, unusual wear, incipient failure, or other problems. In the field of predictive maintenance, the detection of vibrational signatures is a key element of the diagnostic process in which the goal is to identify and remedy incipient problems before a more serious event such as breakdown, failure, or service interruption occurs.

U.S. Pat. No. 8,515,711 to Mitchell et al. proposes that wireless telemetry systems, including point sensors mounted directly on a turbine component, may provide more accurate measurement of component temperature and vibrations. The disclosed system may comprise a diagnostic system that combines the high fidelity data obtained by the point sensors with the broad area data associated with the same components and obtained simultaneously by surface measurement techniques. Calibration of the surface measurement techniques via point sensors located in the field of view on the same components may result in high fidelity data being obtained from a large surface area of the turbine components.

U.S. Pat. No. 9,006,617 to Mullen describes a monitoring system for monitoring the temperature and vibration of equipment, comprising a central digital computer, a MESH communication network, a plurality of heating elements for heating the equipment, and temperature/vibration sensors adapted to measure the temperature of the equipment. The central computer uses the data it receives from the other elements of the monitoring system to determine when the equipment is not at the correct temperature/vibration and diagnoses the reason why.

U.S. Pat. No. 8,924,163 to Hudson et al. discloses a vibration data collection and rotating machinery fault diagnostic instrument that includes a machine setup engine, a measurement engine, a diagnostic engine, a measurement user interface module, a machine setup user interface module, and a diagnostic user interface module. The means of acquiring vibration data are disclosed to be either single-axis or tri-axial accelerometers.

It has long been known that one can analyze the current in a motor to probe various conditions of the motor and equipment that is driven by the motor, using various signature analysis techniques. U.S. Pat. No. 6,774,601 to Swartz et al. discloses a system and method for predicting mechanical failures in machinery driven by induction motors by using the motor as a diagnostic tool to detect present mechanical disturbances. The motor is monitored during operation to avoid down-time. The motor's torque fluctuations are used as an indicator of early-stage mechanical failures in the machinery. The motor's torque fluctuations are determined using indirect sensing techniques that are less expensive and less intrusive than previously known. More specifically, torque is derived from easily and inexpensively measurable parameters, such as motor slip and phase angle. Current operation is compared to known normal operation. Variations of the motor's characteristics from the known baseline indicate an actual or approaching mechanical failure. "Experimental Fractals" are disclosed that visually represent a current state of the monitored machinery and allow for visual comparison to a baseline for detection of mechanical failures. Future failures are forecast by extrapolating a derived trend. U.S. Pat. No. 6,727,725 to Devaney et al. discloses a method to detect motor bearing damage using wavelet analysis of the motor current transient during startup.

Each of the foregoing methods relies on having physical contact with the machine system, either in the form of mechanical accelerometers affixed to the machinery, or by an electrical diagnostic connection in the power line. Each method also requires a specific physical solution for a specific component Many industrial processes involve moving components or workpieces that may vibrate in characteristic (and possibly diagnostic) patterns, but are not amenable to physical contact. Examples include: a moving paper web, either in raw papermaking or in printing operations, moving sheet metal in rolling, heat treating, and finishing operations; moving items on a conveyor; rolling components such as individual rollers that support an elevated conveyor, moving extruded products, such as metal wire, polymer tubes, and the like. It will be appreciated that in each of these situations, important process control and/or predictive maintenance information may be found.

For all of the foregoing reasons, what is needed is a general, non-contacting method for analyzing general vibration processes, particularly in a factory or production environment, that does not need to be custom-built or installed on one particular piece of equipment and may be conveniently deployed on an ad hoc basis to create and maintain a database of historical vibration data for any selected number of individual equipment components or process points.

Objects and Advantages

Objects of the present invention include the following: providing a non-contact vibration analysis system for machinery; providing a flexible predictive maintenance tool for a manufacturing environment; providing a diagnostic tool that uses vibrations in a moving web to provide process diagnostics or controls; and, providing a video-based tool for determining periodic motions in machinery without the need for edge visualization or other specific feature analysis. These and other objects and advantages of the invention will become apparent from consideration of the following specification, read in conjunction with the drawings.

SUMMARY OF THE INVENTION

According to one aspect of the invention, an apparatus for analyzing periodic motions in machinery comprises:
 a video acquisition device positioned at a selected distance from a machine component and having an unobstructed view of a selected portion of the component;
 a data analysis system including a processor and memory to:
  analyze the video file by an adaptive array comparison procedure,
  calculate a parameter characteristic of physical movement of the selected component as a function of time and determine the periodicity thereof,
  time-stamp the video file and the determined periodicity associated therewith; and,
 a data storage system to archive the time stamped images and the physical movement data for later retrieval.

According to another aspect of the invention, a method for monitoring machinery comprises:
 positioning a video acquisition device at a selected distance from machine component and having an unobstructed view of a selected portion of the component;
 providing a data analysis system including a processor and memory to analyze the acquired video file and calculate a parameter characteristic of a physical movement of the selected portion of the component as a function of time and determine the periodicity thereof;
 time-stamping the video file and the determined periodicity associated therewith; and,
 archiving the time stamped images and the associated physical displacement data in a data storage system for later retrieval.

According to another aspect of the invention, an apparatus for monitoring machine components comprises:
 a device for acquiring video files;
 a data analysis system including a processor and memory;
 a computer program operating in the processor to analyze the video images, identify an area in the images where periodic movements associated with a mechanical vibration may be detected and quantified; and,
 an interface in which the quantified vibration information may be displayed as a function of time, and optionally, at least one video frame corresponding to a selected time in the information display.

According to another aspect of the invention, a method for monitoring machinery comprises:
 acquiring a video file of a selected machine component;
 providing a data analysis system including a processor and memory to analyze the acquired video file and calculate a parameter characteristic of a mechanical vibration of the selected component as a function of time and determine the periodicity thereof;
 time-stamping the video file and the determined periodicity associated therewith; and,
 providing a user interface in which the quantified vibration information may be displayed as a function of time, along with at least one video frame corresponding to a selected time in the information display.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting embodiments illustrated in the drawing figures, wherein like numerals (if they occur in more than one view) designate the same elements. The features in the drawings are not necessarily drawn to scale.

FIGS. 14A-14D illustrate the steps in an exemplary analysis for the specific case of respiration. 14A shows the result using a four-frame separation; 14B shows eight-frame separation; 14C shows nine-frame separation; and 14D shows nine-frame separation but starting with a different initial frame.

FIG. 18A shows a video frame of a bridge after a truck (not shown) has passed over it. FIG. 18B shows a single phase mask at 2.25 Hz, which is the fundamental frequency of the bridge. FIG. 18C shows the same phase mask but multiplied by the intensity of the movement at each pixel.

FIG. 19A shows a video frame of a motor that is driving a shaft and flywheel (not shown). FIG. 19B shows another frame in the amplified video clip, representing the point of maximum displacement relative to the frame in FIG. 19A.

FIG. 20A shows 20A shows idealized and non-ideal edges moving to the right. FIG. 20B shows the non-ideal edge moving to the right with amplification factors indicated. FIG. 20C shows the edge moving to the left with amplification factors indicated

DETAILED DESCRIPTION OF THE INVENTION

Figure 1:
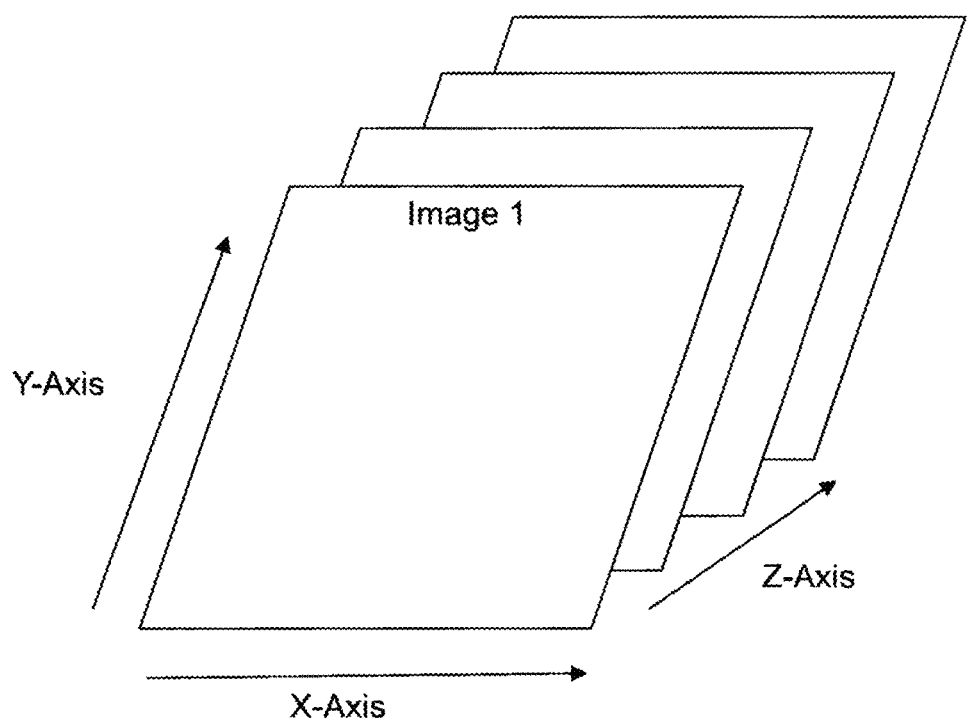
FIG. 1 illustrates schematically the arrangement of video data into a three-dimensional array where x, y are spatial coordinates in a video image and z is time.

The invention is a non-contacting system to observe machinery components using a video camera, find areas of maximum movement and characterize the periodic behavior of those movements (e.g., amplitude, phase, and waveform). The data may be time-stamped and archived for later comparison to other similar equipment or to other data taken from the same component at a different time or under different conditions, to provide knowledge to a predictive maintenance system. The system may include a graphical user interface (GUI), which may display various parameters relating to the measured vibration data, a frame or frames from the video input file, phase masks and motion amplification, time stamps or other identifying information, and user-entered information describing relevant conditions (speed, power level, load, time of day, etc.). It may further allow the user to draw a perimeter or region of interest within the video frame so that analysis may be focused on that region and extraneous movements elsewhere in the frame may be ignored. The system may include an archived database, with which the user can compare historical data in order to determine trends and warnings of machine deterioration, wear of bearings and couplings, loose components, or other symptoms of the need for maintenance before a failure, shutdown, or other catastrophic event can occur.

The invention uses several novel techniques to:
1. Analyze the video file by an adaptive array comparison technique to find a selected number of pixels that have the most variation over time, i.e., the most physical movement.
2. Find the best frames to use (i.e., optimal frame spacing) to maximize the frame differences and best determine the periodicity of the vibration.
3. Apply various mathematical functions, such as fast Fourier transform analysis (FFT) to derive richer physical information from the observed vibration waveform.

As used herein, the terms "machine", "machinery", and "machine component" are intended to be taken in their broadest sense, to include any mechanical component that may exhibit some periodic movements. It includes, for example, motors of all kinds (electrical, internal combustion, turbines), components and linkages connected to or driven by motors; machine tools, grinding wheels and tool bits; electrical and hydraulic actuators; pumps, blowers, fans, pipes, ducts, and other fluid- or air-handling equipment; conveyors and materials or components conveyed thereon; and any parts, products, and workpieces that are moving through a production environment. Examples of the latter include paper moving through a papermaking machine or reduction line; paper or plastic sheet moving through a printing process; sheet metal being rolled, coated, treated, galvanized, hot-dipped, or otherwise handled in a continuous or semi-continuous form; wire or polymer fibers being drawn or extruded; and woven and nonwoven fabric being produced, dyed, printed on, or cut. It may also include components that are not directly driven or intended to move, but which are subject to incidental vibrational inputs, such as in a motor vehicle that are incidentally vibrated by the engine or by movement on a road.

As used herein, the term "vibration" refers to any physical movement that may be characterized by some periodic change of position as a function of time. Vibrations may be periodic, such as, e.g., sinusoidal, symmetric sawtooth, asymmetric sawtooth, or they may be aperiodic or noisy. Vibrations may have any waveform, which may include waveforms characteristic of superimposed vibrations of different frequencies, amplitudes, and phases.

In the examples that follow, various aspects of the invention will be made clearer, and applications to various monitoring problems will be illustrated. These examples are not intended to restrict the scope of the invention to the particular implementations described.

Method of Adaptive Array Comparison

Example

One way Applicants have developed to analyze a video stream to extract waveform information is Adaptive Array Comparison, which may be described generally as follows: A video signal includes multiple frames separated in time and each frame includes multiple pixels. Each pixel value in a particular frame is compared to the values of corresponding pixels in different frames of the video signal to search for periodic signals occurring at the pixel locations over time. Periodic signals are defined in time with a maximum and minimum peaks. These two locations give the maximized absolute value in the difference in two locations of the periodic signals. This fact can be exploited to filter and locate pixel locations where the periodic signal gives the largest signal to background or signal-to-noise in a scene or image sequence. In the case of human respiration we know the adult rate typically lies in the approximate range of 12-20 breaths per minute. This corresponds to 0.25 to 0.33 Hz. A medium rate would be 16 breaths per minute or 0.27 Hz. For a 15 fps camera that corresponds to a breath every 56.25 frames. This would tell us that a video of a person breathing may include periodic signals at certain pixels having a maximum and minimum at a difference of approximately 28 frames apart. This is the initial frame difference we use to locate the best pixels to track. We difference several series of images at this separation, meaning the value at each pixel location in one frame is subtracted from the value at the corresponding pixel location at a second frame. Then, the second frame is differenced with a third frame and so on. For each pixel location, the absolute values of their differences are added together. Then some number of pixels with the highest sum of differences are selected to be tracked. There is the potential that the chosen frames happen to be 90 degrees (or some other phase shift) out of phase with a max and min; so in the event that no initial peaks are found, we recalculate with a 90 degree phase shift (or some other phase shift). Once we find the correct pixels to track, we then begin peak counting for each selected pixel, noting the phase of the waveform. Once we have sufficiently determined the precise phase and frequency of the waveform, we recalibrate, making sure to frame difference such that the number of frames between differences exactly equals the difference between a max and min of the waveform, as well as starting in phase so the difference is aligned with the max and min. The processor runs the code to do this like any other programs, although a specialized piece of hardware specifically designed to do this is not necessarily used (in contrast to the way decoding HD video is typically done).

Applicant has found that the foregoing method adapts to a particular component's waveform even if it changes. In the example of machinery, different frequency rates can be chosen to start with, based on some rudimentary knowledge of the equipment or previously stored user data. For example, passive electrical equipment might be expected have a vibrational displacement corresponding to 60 Hz or some harmonic thereof; a motor or linkage might have most of its vibration at a frequency associated with its rotational speed. The inventive method inherently filters unwanted frequencies. Because of the selected time difference between frames we reject signals associated with frequencies other than those related to the process we are monitoring.

Example

An image sequence is obtained through a video camera and stored into memory. A video sequence as shown in FIG. 1 has dimensions of space in the x and y axis while having the dimension of time in the z axis and can be thought of as a 3-D data space. The video sequence contains a periodic or recurring motion of interest that is to be extracted from the data set. For example, a feature of interest may be occurring at a given pixel and we may be interested in monitoring that feature. We can use its temporal behavior to find and locate that pixel without any knowledge of the scene, the surrounding pixels, the spatial characteristic of the local pixels or where that pixel may be.

Method of Adaptive Array Comparison for the Detection and Characterization of Periodic Motion

Example

Mathematical Description

An image frame is defined as an X-Y matrix. A video file is a set of image frames defining an X-Y-t matrix.

For each pixel (i,j) one can calculate the difference $(D_{i,j})^{M,N}$ between the value at pixel (i,j) in one frame and the value in another frame, where M is the starting frame number and N is the spacing between the two frames. So $(D_{2,3})^{4,9}$ would be the difference in value or intensity at pixel (2,3) in frame 4 compared to that in frame 13.

The difference matrix is then summed (preferably in quadrature) to yield the total difference in pixel intensities between frames M and M+N. Difference matrices are calculated for various values of M and N, to find M and N that give the highest value of summed differences. Then a selected number of pixels (i,j) having the greatest difference are chosen and their intensities are tracked over time to determine the periodicity of movement.

There is generally a limit on how long one does this. For example, at 15 fps for 20 sec there are 300 frames, so if N is 10 we difference 29 times (accounting for the ends) or less as M is increased.

Once this is done initially and we have found the location of a peak and the peak separation we redo the calibration with a specific M and N to get it exactly on the peak. M would now be the frame number where an expected max or min occurs and N would be the value of ½ of a waveform. This introduces the novel aspect that the process becomes essentially adaptive.

Example

The method and functions of Adaptive Array Comparison may be described as follows:
1. Video Sequence comes in at some frames per second (fps)
2. Some seconds of that data is continually buffered. (Previous frames are overwritten with new frames.) These are the frames we process.
3. From the buffered frames [1], [2], . . . [n] we select a multiple of frame differences N to calculate, e.g. every $4^{th}$ frame (N=4) or every $5^{th}$ frame (N=5), etc. This allows us to find the best periodic motion rate. We select the time range between frames based on the range of periodic motion we are interested in finding. This also acts as a band pass filter giving preference to the periodic motion rate within this range.
4. We also offset these frames, say, starting with the $1^{st}$ frame, then the second, etc. This allows us to find the best phase. So for example if we are subtracting every $4^{th}$ frame, we first would do the $1^{st}$ frame minus the $5^{th}$, the $5^{th}$ minus the $9^{th}$, and so on. Then we would do the $2^{nd}$ frame minus the $6^{th}$ frame, then the $6^{th}$ frame minus the $10^{th}$.
5. For each test, frame differencing is conducted for some number of frames. For example, 11 frames may be used and 10 frame differences will be calculated. Each frame difference will be an array of absolute value numbers with each position in the array corresponding to a pixel location.
6. After 10 frame differences are calculated the square of the frame difference arrays are added together to produce a total frame difference array. Then the total frame difference array is analyzed to find the array locations having the largest values. For example, the ten largest values in the array may be found and the array locations containing those values are recorded. When we subtract the frames we add all the differenced frames from the buffered video in quadrature, meaning we square the difference values so that negative and positive differences don't cancel. Motion in opposite direction shows up in the difference frame with an opposite sign but we want that to add positively, otherwise back and forth motion can show as zero in the sum of the differenced frames.

7. From all the total frame difference arrays across all the multiples and offsets we find a selected number of pixels that have the largest values, say, the brightest 10 pixels. These pixels represent the largest periodic motions in the scene that are between the rate boundaries set in Step 3.

8. Those pixels' values are tracked over time and this will plot the motion waveform. The signals from the tracked pixels are not necessarily in phase. Any two signals could be 180 degrees out of phase and still provide the same information about the existence and the frequency of the same time periodic signal. For example, the signals of all pixels could be out of phase with all other signals, but still correspond to breathing of a subject. Thus the frequency of each signal would be the same.

9. From the motion waveform we determine the rate and phase. In terms of frame differencing this translates to the peaks in the waveform occurring every $N^{th}$ frame and the waveform starts at frame M.

10. From the information in Step 9 the Adaptive Array Comparison method adapts since we know where the peaks start and how many frames apart they are.

11. Now we subtract frames with a separation exactly equal to the separation between a maximum and minimum in the waveform. We also make sure to start this process exactly on a peak or minimum. This optimizes the rate and phase to precisely select the motion waveform.

12. This process can be repeated based on a number of factors:

a. Time—The method can reiterate every n seconds to ensure it is optimized for the existing waveform.

b. When there is a large excursion in the measured waveform the process can restart as this can be due to a motion event.

c. The process can restart based on a trigger from an external motion detection method.

d. The process can be restarted on buffered data (the 20 seconds of previous video) when an alarm is triggered, (for example, no peaks are detected) to ensure the alarm is accurate. For example, if the waveform is accidentally lost this step could check the last 20 seconds of data to see if the waveform can be detected in another pixel or set of pixels.

Example

Figure 2:
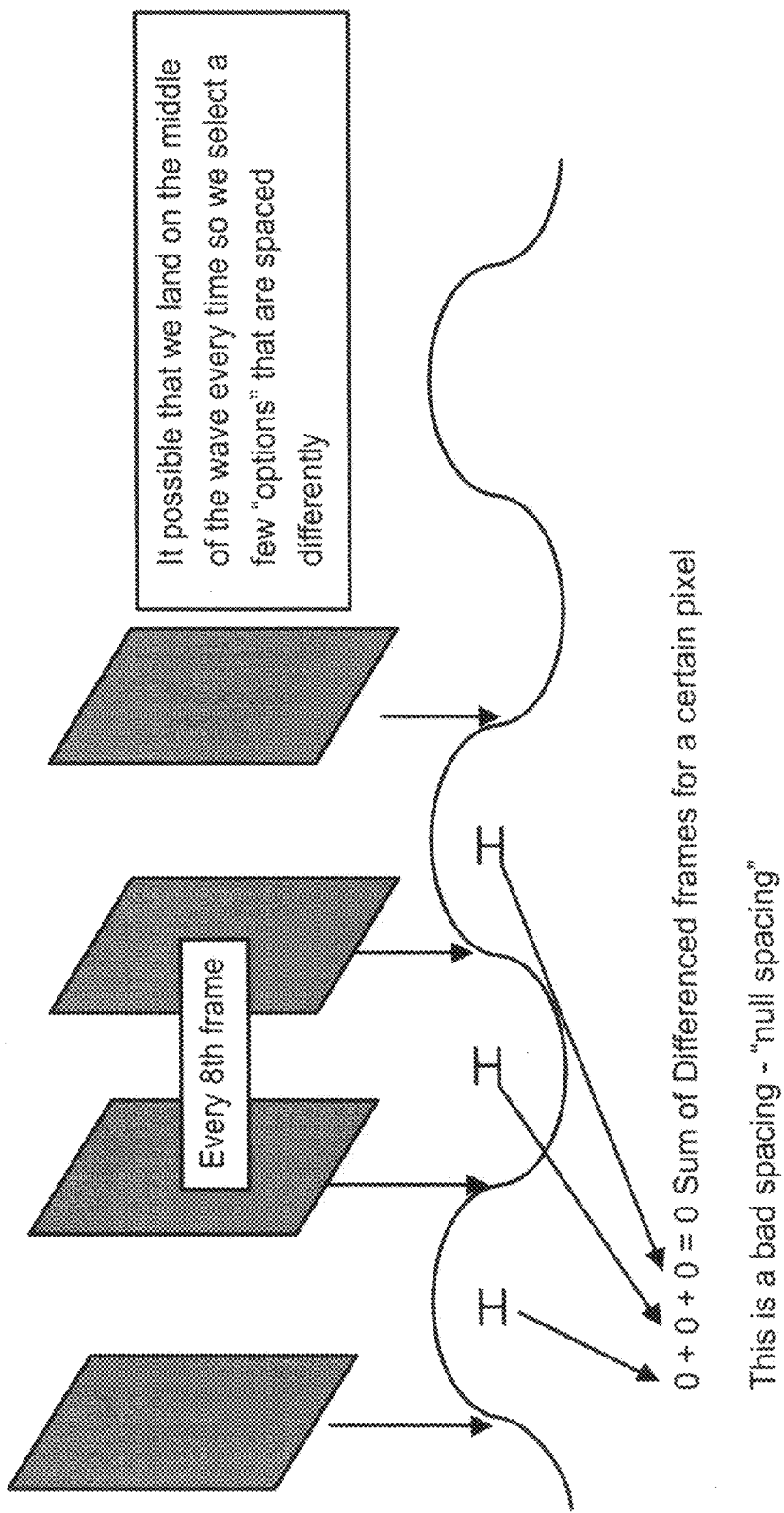
FIG. 2 illustrates the result when the frame spacing is non-optimal, in this case, every 8th frame (N=8).
Figure 3:
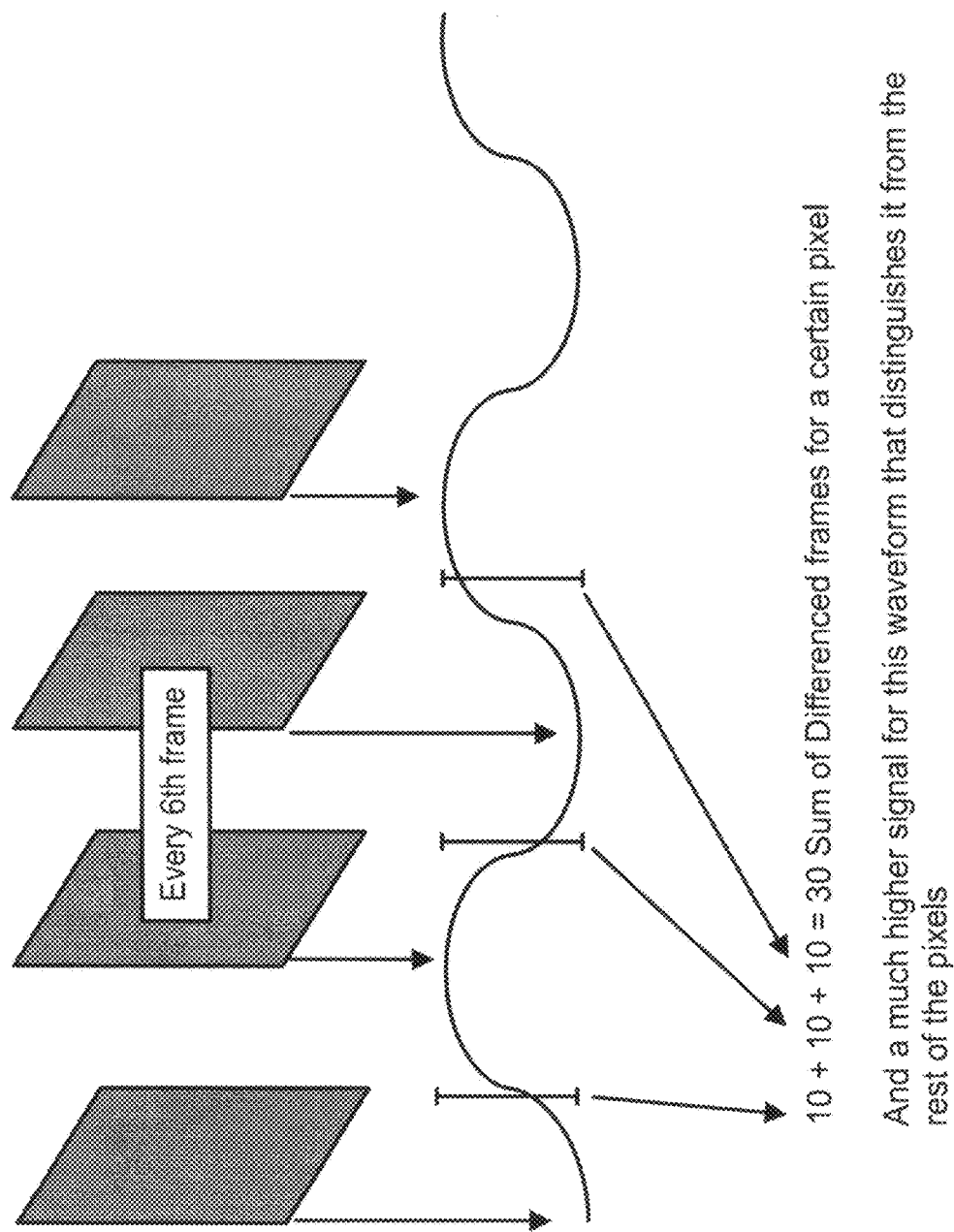
FIG. 3 illustrates the result when the spacing is more nearly optimal, in this case, every $6^{th}$ frame (N=6).

FIGS. 2 and 3 illustrate how the system selects the frame spacing by trying two different spacings and comparing the magnitude of the peak differences. In FIG. 2, every $8^{th}$ frame is used; this turns out to be a bad or "null" spacing, as the sum of differenced frames for a given pixel is zero. When the spacing is changed to every $6^{th}$ frame, the sum of differenced frames for a given pixel is 30, indicating a much higher signal for this waveform that distinguishes it from the rest of the pixels.

So therefore, we would try a multiple of spacings that represent a reasonable range of vibration rates. We would also offset them or change the phase because the best spacing that perfectly finds the peaks and valleys is also a "null set". Now we know where to look when this gives us the pixel with the largest sum of the differences. From this pixel we track and locate the peaks and valleys of the waveform. Then we adapt to the individual component's waveform with the next calibration.

Example

Figure 4:
FIG. 4 illustrates a summed frame of differenced frames from 20 seconds of video data. Note the method isolated motions associated with the breathing based on the selected frame number separation as indicated by the darkest pixels in the summed frame.

FIG. 4 illustrates the summed frame of differenced frames from 20 seconds of video data collected on a human subject. Note the method has successfully isolated motions associated with the breathing based on the selected frame number separation: here the darkest pixels identify the location of greatest motion found in the chest region from the up/down right/left motion of breathing as seen by the camera. These are the pixels that would then be tracked to determine the breathing waveform. It is important to emphasize that the data presentation in FIG. 4 is not an image per se, but rather simply a graphical display of the pixels (dark) that show the most movement. It is also important to emphasize that the entire process was conducted by the processor in an essentially autonomous operation.

Example

An explicit example of the calculations can be shown as follows: Let [1] be the first frame of a video sequence, a 640×480 image, so that [1] is a 640×480 array. Likewise [2] would be the second frame making up a new 640×480 array and [3] would be the third. We would like to sum the difference of every x frames. To ensure the difference is positive we subtract the frames, then square the difference, and then take the square root. Finally we sum all of differenced frames.

For example, if we difference every 8 frames the calculation would be of the form:

$$\sqrt{([1]-[9])^2} + \sqrt{([9]-[17])^2} + \sqrt{([17]-[25])^2} + \sqrt{([25]-[33])^2} = [SUM]$$

Other potential applications and features of the invention include the following:

A user defined setting can be selected to narrow the window on which rates to look for, e.g., 60 Hz in the case of equipment running on standard AC power. It will be appreciated that narrowing the window allows the system to converge more quickly on an optimal frame rate, because this reduces the number of iterations the system has to go through, making it quicker and more accurate as the chance of error would be reduced by eliminating certain frequencies.

Information such as a profile of a particular components characteristic vibration rate, may be stored and later retrieved so the device has a better range of expected rates to look for a priori. In this case the user selects a profile that the device has gathered over previous uses or parameters that were previously entered.

Sections of the video scene may be selected to narrow the search. For example, if the video camera is looking at the edge of a moving paper web, the user interface might allow the user to draw a box (e.g., on a touch screen) to select only the sheet of paper, eliminating the rest of the production environment. Eliminating extraneous parts of the image from consideration will allow the calculations and optimization to proceed more quickly.

One can isolate periodic motion by selecting the range the motion is expected to be in. For example, a particular pump might have a standard speed at which it rotates or reciprocates, which will suggest a reasonable range of frequencies to start with.

The data can be used with a standard peak finding method to determine the max and mins of the waveform.

Example

Figure 5:
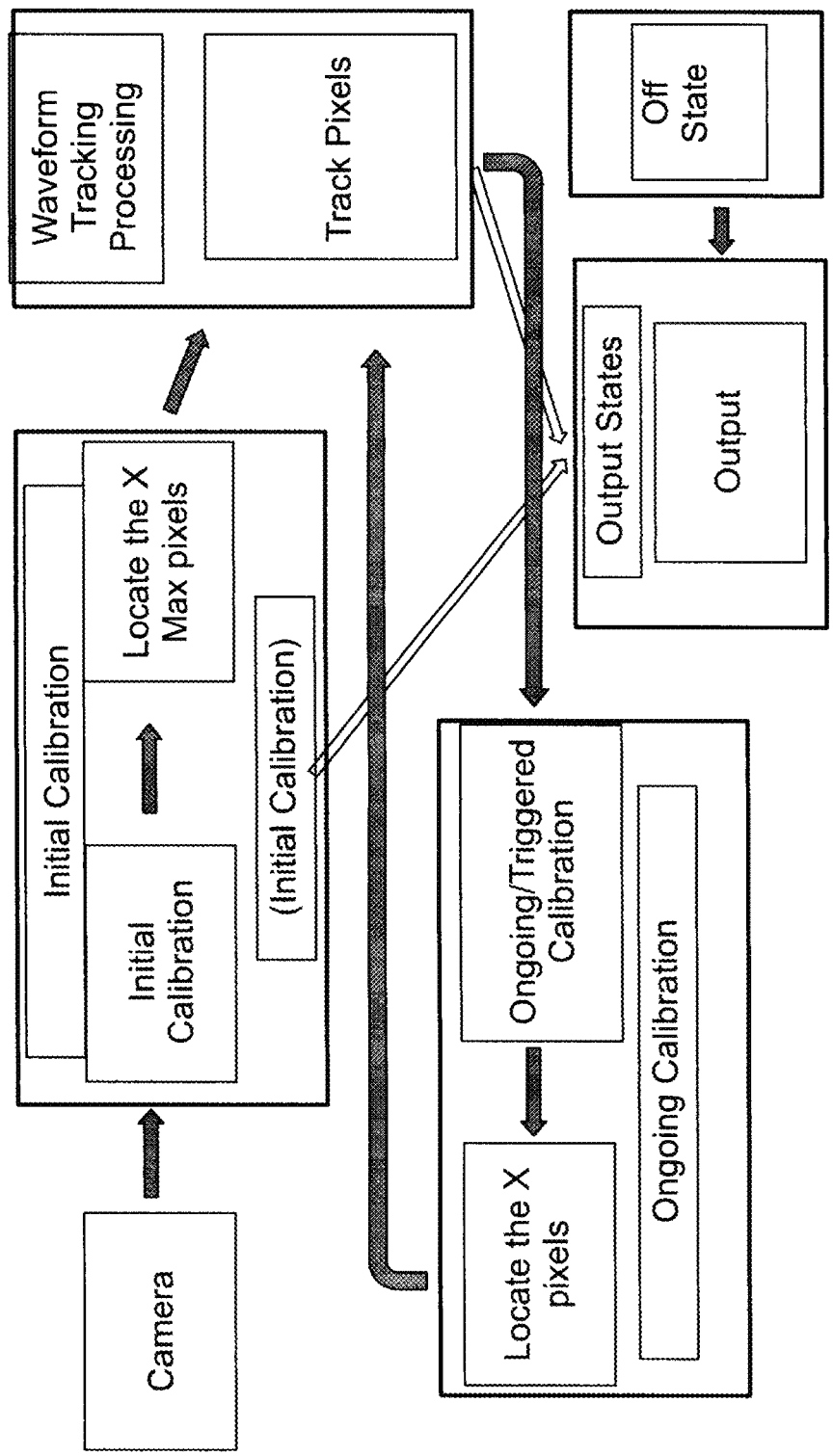
FIG. 5 illustrates a simplified flow chart of the basic camera operation and analysis done in a completely automated process.

FIG. 5 presents a simplified flow chart of the basic camera operation and analysis done in a completely automated process. The input video may be MPEG1 simple profile or MJPEG from, e.g., a USB webcam or similar source. The initial calibration subroutine, using 20 s of video, locates the 5 pixels with the greatest values in difference matrix, and establishes State 0, or initial calibration. The waveform tracking and processing subroutine tracks pixels, continuously outputs the last N values of the pixels determined to be the greatest from the difference matrix; processing is done on waveform to determine output states. States 1-3 will be determined in this routine based on processing of the waveforms. An ongoing calibration subroutine is continuously looped; this uses 60 s of frames, summing the difference of frames and locating the five pixels with greatest values in difference matrix. Five output states are continually outputted from the subroutines through a physical channel. Off State condition may be determined by a selected trigger, implemented either in hardware or software.

Example

Calibration Subroutine

A subroutine recalibrates the location to find the best pixels. This consists of going through the process of frame differencing again and locating the 15 highest valued pixels in the summed array. The duration of the calibration can be programmatically controlled as well as the frame numbers to difference as a result they may vary. For example we choose to difference every 4 frames of a 16 fps camera for 40 seconds resulting in 160 differenced frames. Note this in different than the initial calibration since it is limited to 20 seconds.

This recalibration process continually goes on in the background while the waveforms are being outputted from the pixels and the peak finding is performed.

It is important to keep in mind that the mathematical techniques of the present invention derive parametric outputs whether or not an image is ever created or portrayed. Thus, techniques of the present invention may be used with monitors that do not display images, do not recognize objects, and do not have frequent human observation or similar participation. For example, the present invention may output a commonly reported characteristic such as a breathing rate or heart pulse rate or phase or a lag interval or a dimension of a periodically moving object or a period of a motion, or a timing or a motion or other information associated with a periodic motion event without displaying an image thereof. Conversely, in some examples, the user interface may include actual video images, which may be selected to correspond to a particular point in time when an output parameter has a particular value or the waveform displays a particular feature (e.g., an episode when unusual vibrations or some instability appeared temporarily).

As used herein, the term "video" describes any data set representing a series of digital (i.e., pixelated) images of a scene, taken at fixed time intervals, so that the data represent points in X-Y-t space. The image may represent a pattern of reflected and/or emitted visible light, UV, IR, X-rays, gamma rays, or other electromagnetic radiation detected by a two-dimensional position-sensitive detector. Although certain standard file types have been described in some of the examples, the invention is not limited to any particular frame rate or file format.

It will be further appreciated that the invention is not limited to any particular type of image acquisition hardware; video cameras, webcams, digital cameras integral in cell phones, etc., may also be used to generate the raw data files. Alternatively, the raw video may be generated elsewhere and downloaded to the processor from a USB memory device, a CD or DVD, or via an ethernet or wireless connection. The digital imaging device may further include any suitable lenses or other optical components, such as telescopes, microscopes, etc., as are well known in the art. In particular, the invention may be used for examining periodic movement in small MEMS devices or micro-actuators, which could be observed using a video microscope for quality control or other purposes. Adapted to a telescope, the invention could be used, e.g., to study vibrations in ships, helicopters, missiles, etc.

Many examples of the present invention are completely general in that they do not require or insist upon a blob that must be identified with an object in the field of view or with a contour segment that must be associated with an object in the field of view.

Techniques of the present invention may be applied to a variety of imaging modalities, including visible imaging, thermal imaging, multispectral imaging, or hyperspectral imaging. In fact these are entirely different and independent media having different sources and different mechanisms and different physical significances. However, the techniques for measuring motion remain the same for any spectral ranges. For example, the use of visible images of an object of interest overlaid (or interleaved, overlapped, interspersed, approximately synchronized, or truly simultaneous) with near or far infrared images may yield two effectively independent views of an object of interest. If reflected visible light reveals a periodic motion which may be associated with a structural vibration or some other periodic motion, and a thermal image (perhaps due to friction or an electrical problem) reveals a similar periodic motion location proximate to the visible finding and similar in phase, frequency, or amplitude, or all three, then this improves the likelihood of an accurate result rather than a false positive or false negative finding.

As noted above, the imaging systems may have multiple inputs. These may comprise two visible cameras, an infrared imager and a visible camera, a camera and another input other than an imager such as an ultrasonic sensor or a temperature or a pulse monitor or some other combination of two or more imaging devices.

Example

In a system in which material is being processed in the form of a moving web, e.g., papermaking, it may be advantageous to position two video acquisition systems opposite one another so that each is recording images of opposite edges of the web. In this setup, it will generally be preferable to have both systems synchronized with a common time stamp so that coupled vibration phenomena may be detected and quantified.

The rate of video frame acquisition may be adjusted, e.g., to correspond with a naturally-repeating feature on the moving web, such as a printed page. In this way, every frame would capture substantially the same view, and periodic vibrations may be more easily discerned. In a case such as the cold-rolling of metal sheet products, the frame rate may be adjusted to correspond to the linear equivalent of one revolution of the processing rolls, so each frame represents a part of the sheet that contacted the same area on the roller.

The inventive technique is not limited to a particular wavelength of light. Different colors are represented by different wavelengths of light, e.g. 550 nm is green. Amplitude changes that are detected by this technique can be restricted to a single wavelength of light or represent a summed intensity change over multiple wavelengths. Each wavelength can be measured independently or together (mono grayscale). The inventive technique may, for example, monitor only the green, blue or red wavelength or monitor the sum of all three.

Electromagnetic Wavelength options. In addition the inventive technique is not just limited to visible wavelength of light, but can be used in the near IR, far IR, or UV. The technique could be extended to any sensor type that can measure changes in light levels over time whether from reflective or emissive sources. Visible light is generally although not always measured as a reflection. Thermal IR light is generally but not always an emission from the surface. The invention works regardless of whether or not the target is reflecting or emitting the light.

Sensor selection. The sensor type can be chosen based on the scene or target. For example, if the scene is completely dark, void of a visible light source, a thermal IR sensor may be used to monitor the changes in light levels. Also if a particular material or substance is the target and light level changes are due to a property of interest on the target another sensor type may be chosen. For example, with gas that absorbs in certain wavelengths, or more generally chemicals, a particular sensor that detects those properties may be chosen. For example, one may be interested in using the technique to find an exhaust or chemical leak in the scene based on light intensity changes from the leak specifically associated with the absorption and/or emission at certain wavelengths. Another example may be a flowing liquid that absorbs in certain colors, and that flow changes or pulsing may be indicated by intensity changes in a certain wavelength of light, then a sensor particularly sensitive to that wavelength of light might be chosen.

Interpreting measurement information. The inventive technique can also be used to garner information about the type of change. A particular change using a thermal sensor would indicate that the temperature is changing, whereas a change in color may indicate the target is changing is absorption or emission properties. A change in amplitude could also be indicative in a change in position or vibration, whereas a change in position of the signal being detected from pixel to pixel in time may give information about displacement.

Example

Because temperature is an important factor in predictive maintenance, a GUI may display a video frame of a component along with an IR or thermal image, either separately of as an overlay (which may be calibrated color or grayscale) for a more complete interpretation of the entire data suite.

Comparing multiple measurements. Ratio or comparisons of color changes or amplitudes of certain wavelength can also be used. For example, it may be useful to locate a pixel that changes in intensity from blue to red. This could be indicative of certain properties of interest. An example would be characterizing the uniformity of printing or dyeing on a paper or fabric web. Multiple sensors could be used for this technique or a single sensor with wavelength filters applied (such as a typical color camera). Certain features of interest may be indicated by relationships between multiple sensor sensitivities or wavelength of light.

Redundant and independent inputs. Multiple sensor types or wavelength detections could also provide multiple detections of the same phenomenon increasing the confidence of detection. For example, the light intensity changes due to the periodic vibration of a duct may be detected with a visible or IR camera pointed at the duct wall while another sensor looks at the intensity change in thermal IR from temperature changes around an inlet or outlet of the duct. The technique is then used in both cases to strengthen the detection scheme.

False negative findings. Multiple wavelengths could be used to discern or improve findings which may be false positive and false negative findings and true positive and true negative findings. Intensity shift from multiple wavelength, red, blue, green, IR, etc. could be used in conjunction with each other to improve the signal to noise ratio and also provide multiple independent readings to increase confidence in detection.

Measurement duration. This technique could be used with signals that are repetitive but only over a short time duration, e.g., vibrations that arise in forging or stamping operations. The technique could be applied to shortened windows of time to catch signals that occur only for a set duration. Furthermore it could be used for signals that continually change over time but are ongoing. For example, with a signal that speeds or slows, the time that is used to calibrate or search for a certain intensity change could be shortened to be less than the time change of the signal itself.

Figure 13A:
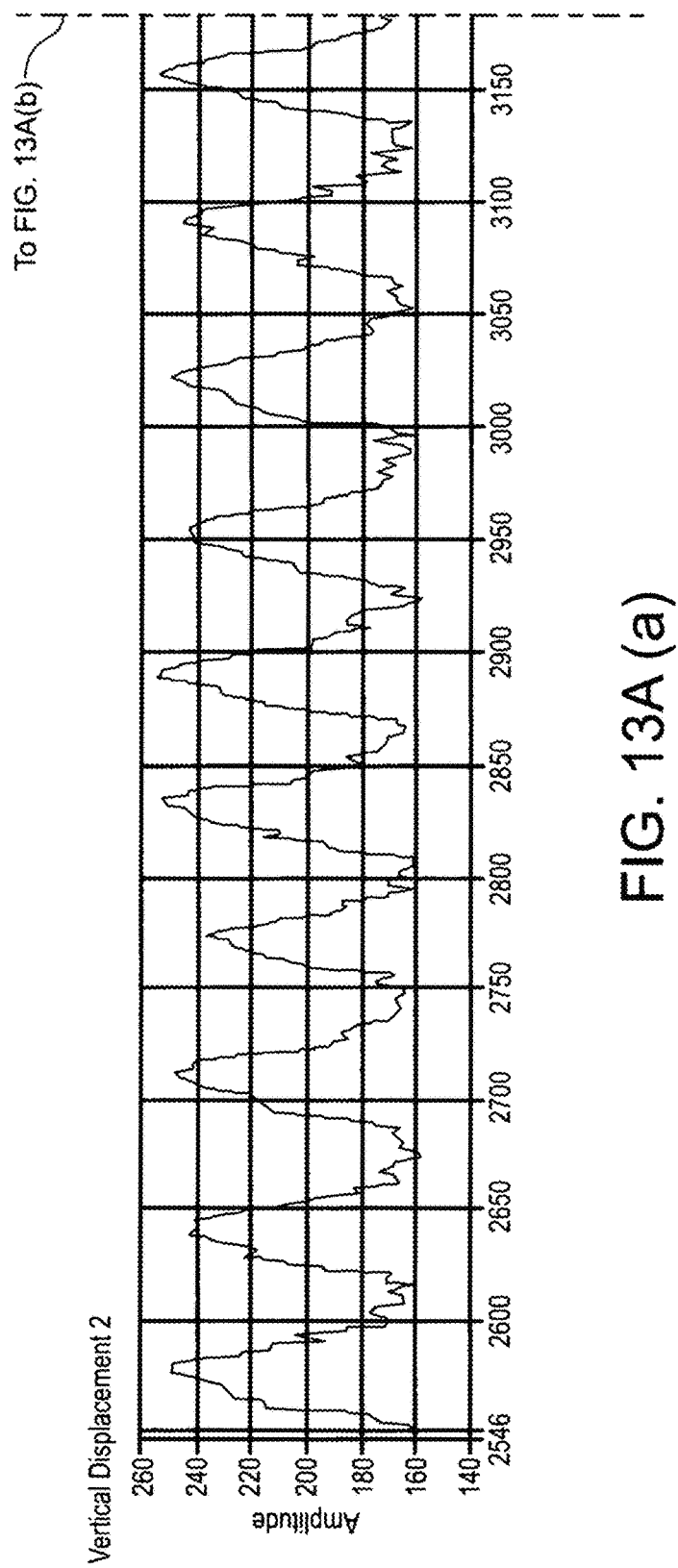
FIG. 13A illustrates a regular or healthy respiration waveform.
Figure 13A:
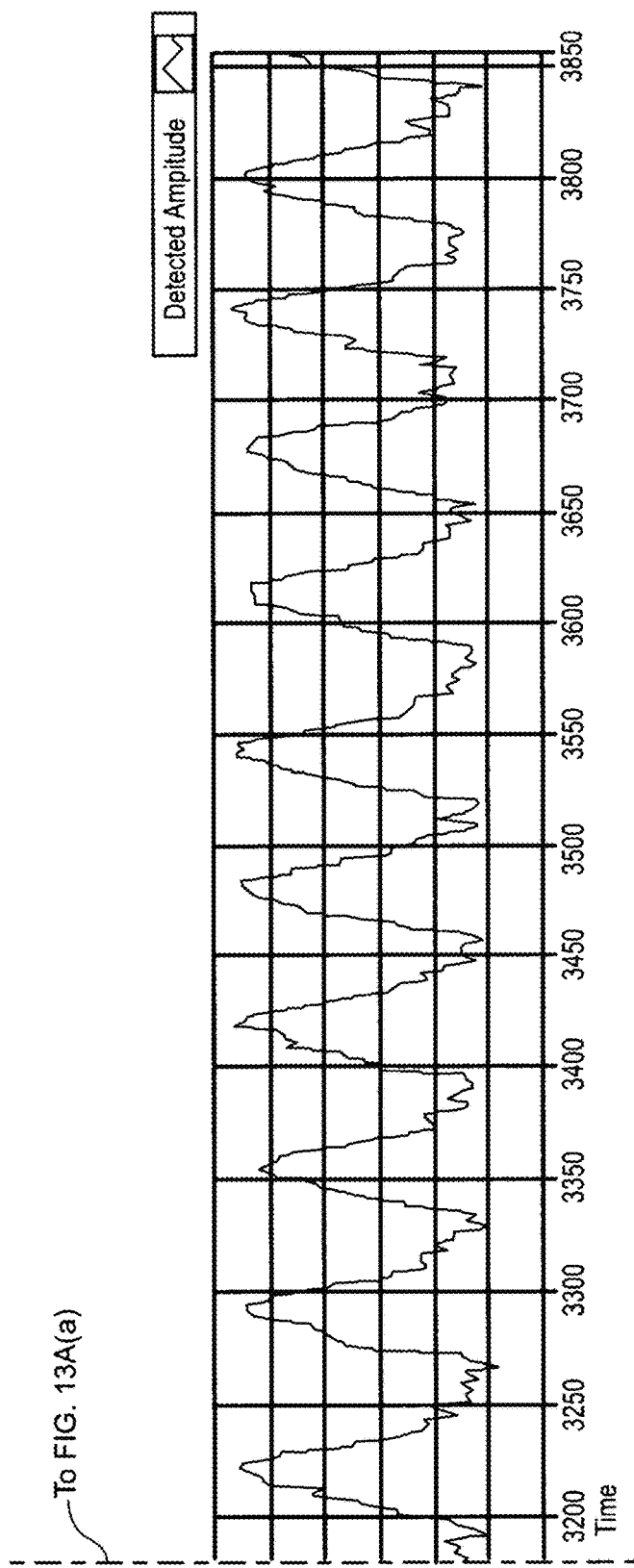
Figure 13B:
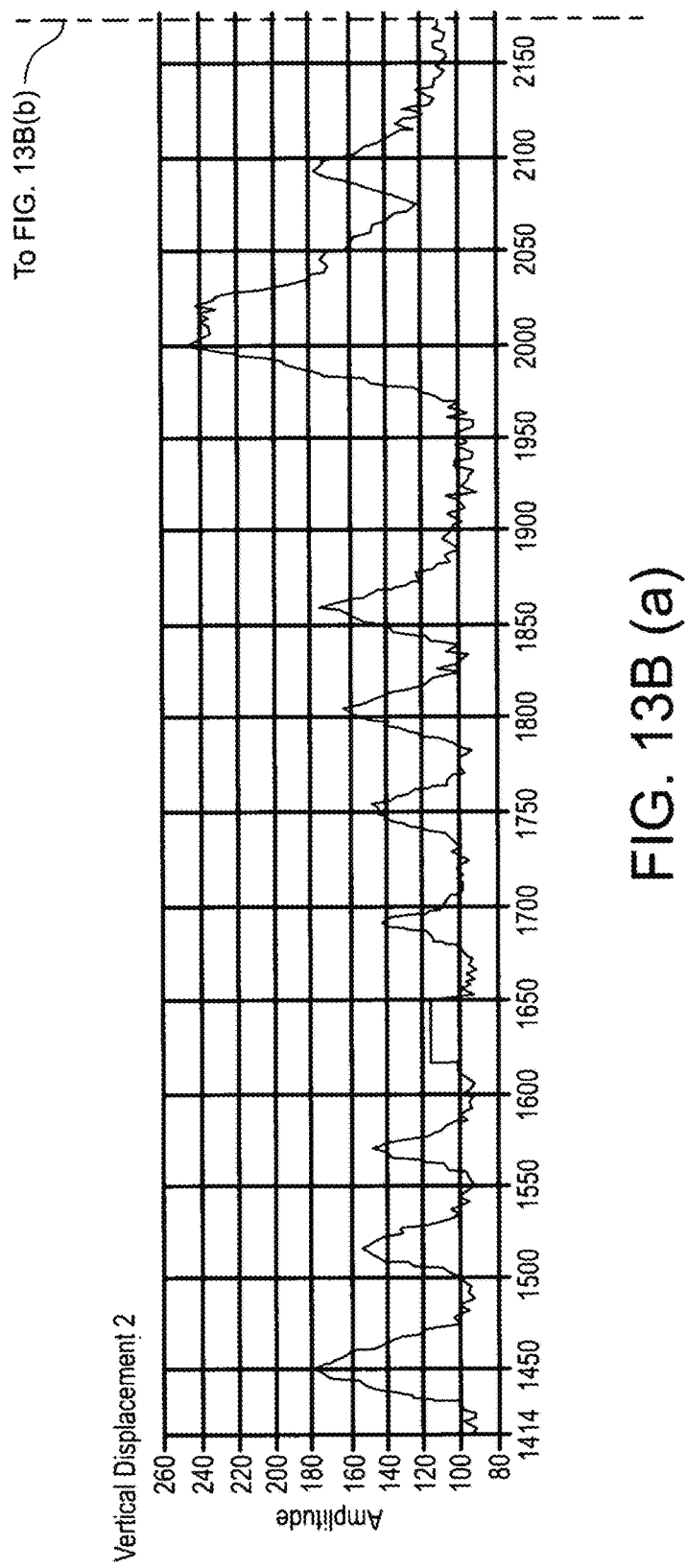
FIG. 13B illustrates an irregular and transient event in an otherwise periodic motion, as detected using the present invention.
Figure 13B:
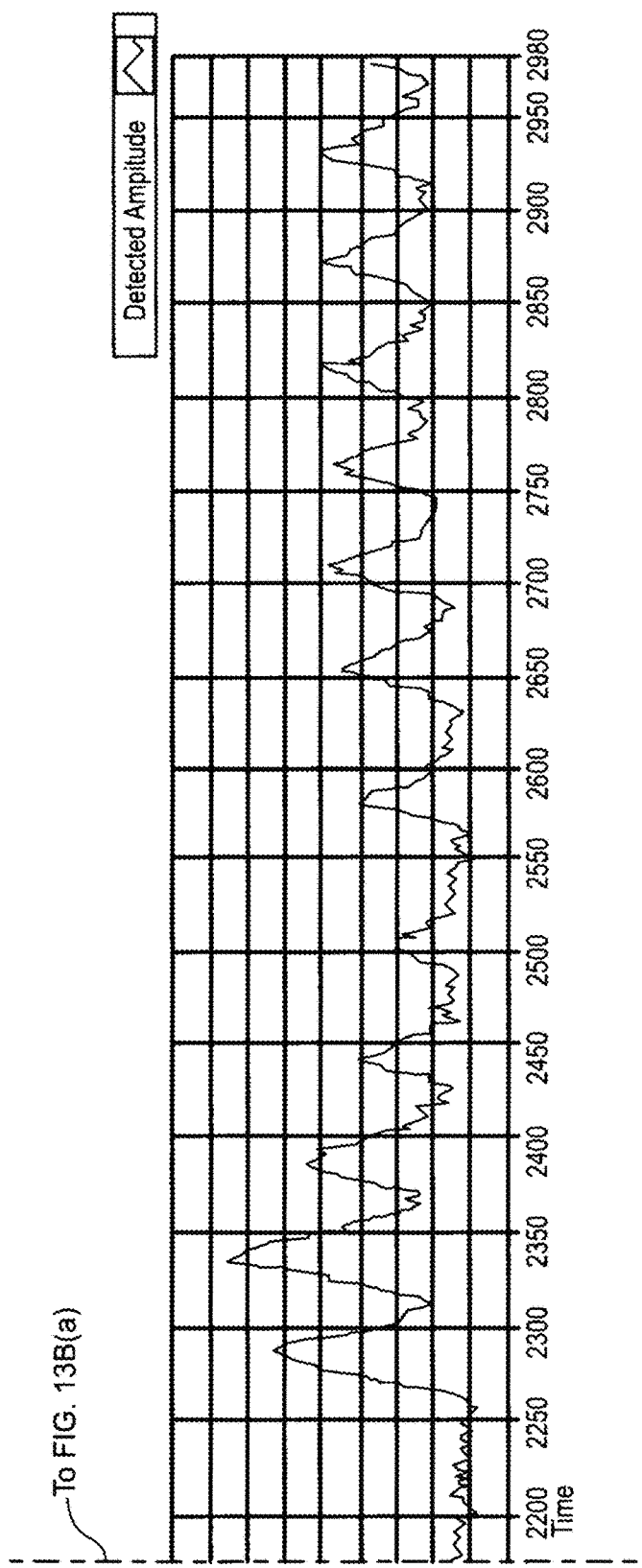

Transient event. Additionally there may be irregular or transient events in a periodic signal. This technique could be used in a short enough time window or in a sufficient sequence of waves to extract the location of a periodic signal in the presence of irregular or transient events. FIG. 13B shows an irregular and transient event in an otherwise periodic motion. If the sample window for the technique described here is properly placed the maximum and minimum of the periodic signal can be located. Multiple phase offset would help to address this issue by building up a pixel's sum of differences at a time that the phase offset for a starting point has brought it past the irregular or transient signal occurrence.

Spatial proximity. This technique can find multiple pixels of interest. Spatial relationships between the pixels of interest can further be exploited. For example, if a larger number of pixels of interest were selected and the vast majority of them were found to be in close proximity to each other that could indicate those pixels are related to the same physical phenomenon. Conversely, if they are spread apart and there appears to be no spatial coherence or statistical meaning among the spatial relationship or they are randomly spaced that could indicate they are not related. Furthermore, this technique could also be used to increase confidence in the signal or improve findings which may be false positive and false negative findings and true positive and true negative findings. For example, in a motor-driven pump, there are likely to be many pixels of interest found near the coupling. We could expect a certain percentage to be heavily localized. If this is not the case it may lower our confidence that the vibrations of the machine are being detected. Conversely, if a large number are heavily centralized we may be more confident we have located a physical region undergoing motion from vibrations. The confidence may be set by a weighted spatial location mean of the pixels or average separation distance, or standard deviation from the spatially averaged locations of the all pixels of interest.

Cycles per minute. Intensity variations for different pixels of interest can be indicative of certain phenomena of interest. By limiting the temporal separation of which the pixels are differenced and the differenced sum is obtained we can filter for phenomena of interest. For example if we are interested in a rotating or reciprocating machine we would preferably limit our frame separation to max and min separation time of waveforms that correspond to the rate of rotation or reciprocation.

Re-calibration—finding a pixel of interest. It is possible after the technique adapts to find the suitable or best separation to get the largest intensity change based on the differencing of max and min frames, a new search can be performed with that knowledge with tighter constraints to search out specifically that waveform. In that sense it is adaptive after it uses more liberal parameters to find the initial signal. It is possible that a user's information or information on a subject or phenomenon may be stored. The technique can now be used with a priori knowledge of rate, phase etc. to speed up finding the pixels of interest. For example, a user may store the profile of a particular machine or class of machines, and the technique is then used with knowledge of that data. That way, fewer cycles need to be performed and a tighter constraint can be placed on the technique to find the pixel of interest.

Visible and infrared photons. Variation in the intensity of pixels may not always result from radiation emitted or reflected by a single object. For example, if something is moving and at a different temperature than the background, that object may move back and forth periodically blocking a small portion of the background. To a thermal sensor, a pixel detecting light in that region will see an increase and decrease in brightness from the object moving back and forth as the object at $T_1$ and then the background at a different temperature $T_2$ are alternately imaged by the pixel.

Multiple cameras. Multiple cameras can be used for multiple detection schemes. They potentially could run at different rates. It is possible to temporally align frames so that certain frames occur at the same time. In this scene the resulting detection of a signal can be temporally aligned as well and correlated. Cameras could potentially be set to image the same field of view. Pixels across multiple cameras or sensors could be correlated so spatial relationships of the pixels in the image of each camera is known.

Other sensors. Other inputs could be correlated to one of more cameras. The detected signal could potentially be correlated to another input signal as well. For example, a prox probe could be used to validate or increase the confidence of a detected signal determined from a pixel of interest from the technique. Tachometers, accelerometers, and tonometers are all examples of types of sensors that could be used in conjunction with the inventive technique. These input signals could also provide frequencies or phase data to allow the system to use tighter constraints to reduce the number of iterations it goes through or immediately determine the proper phase and or frequency from which to select the differenced frames. These inputs also can be used as triggers.

Single pixel and combination of many pixels Techniques of the present invention may be used with the smallest achievable pixel size or may be used with binned pixels where multiple neighboring pixels are collectively associated (mathematically or statistically) to create a larger virtual pixel. This technique may be done on camera or chip or done afterwards in data processing. Binning may be done horizontally, vertically, or both, and may be done proportionately in both directions or disproportionately. Collective association or binning may potentially leave out or skip individual pixels or groups of pixels. For example, one form of collective association may comprise combining a plurality of bright pixels while ignoring some of all of the pixels not determined to be "bright" or "strong" considering a characteristic of interest such as a selected frequency range or amplitude.

Gaining confidence by eliminating false findings. It may be of interest to increase the confidence of the detection by exploring neighboring pixels. Even if those pixels were not chosen as the ones exhibiting the largest motion they can be explored to determine if at least one or more exhibit the same or strongly correlated waveforms to the pixel of interest. If a physical phenomenon that one is trying to detect is expected to be larger than one pixel, it stands to reason that neighboring pixels undergo similar behavior. Thus it will be clear that this could be used to eliminate false positives in a detection scheme.

Multiplexing. The inventive technique can be applied in a single pixel variant in which an optical element would be used in a multiplex mode where the optical element scans the scene and the transducer samples at each point in the scene. An image or array is created from the scanned data. The sampling/scanning rate is contemplated to be high enough to effectively sample the scene at a fast enough rate to see time-varying signals of interest. Once certain pixels of interest are located, the system would then need only scan those pixels until a recalibration is needed.

Searching a plurality of frequencies. One can compare amplitudes of different subtracted frames separation values, or multiple sums of subtracted frames separation values. For example, comparison can be made between the sum of the subtracted frames for separation X and for separation Y. The frame separations are indicative of frequencies. This comparison will allow one to compare amplitudes of signal changes for different frequencies. Multiple frames separation values that give information about amplitudes of a frequency of the signal can be used to construct a frequency spectrum for a single pixel or multiple pixels.

Arrays representing subtracted frames or sums of subtracted frames at certain frame separation values may be indicative of a frequency. Those arrays may be compared to indicate information about the signals. For example, if two arrays are determined that are indicative of frequency $f_1$ and $f_2$, we may compare those two arrays for determine the spatial distance between the phenomenon that is causing the frequencies. In this case the array may be a spatial image.

The following example will more fully illustrate the inventive method, applied specifically to the case of monitoring respiration, as described in Applicant's co-pending application.

Example

Initial calibration with a single frame separation value and starting point for frame differencing does not optimize the differenced values specific to the respiration rate or maximum and minimum values in the chest motion. To solve this we select multiple frame separation values, all at multiple starting points, to ensure that we find the optimized signal of interest. A series of waveforms, FIGS. 14A-14D demonstrates this principle.

Here we see that at 4 frames of separation, FIG. 14A, the separation does not align with the maximum and minimum peaks in the waveform. Aligning with the maximum and minimum peaks would give the strongest signal indicating that the right separation or rate has been found.

FIG. 14B shows the effect of changing the separation between differenced frames to every 8 frames. One can see that this is better but not quite optimal. Next consider 9 frames, FIG. 14C. To ensure that all possibilities are considered we want the option to select a range for frame separations to subtract as well as the increments in spacing. For example, we subtract from every 2 to 30 frames in increments of 4, or generally we subtract from $N_1$ to $N_n$ in frame separations in increments of $\Delta N$.

In addition to frame separation values, the starting point (referred to as phase in wave mathematics) plays a role in finding the correct frame.

Considering again the case of 9 frames, as shown, it was the correct separation to subtract to find the maximum difference in frames since it aligned with the maximum and minimum in the waveform. Now we choose a new starting point and how it affects the results.

In FIG. 14D, we see that offsetting the starting point to frame number 5 misaligns the 9 frame separation so that it no longer lines up with the maximum and minimum of the waveform. So in addition to doing a multitude of separations, for every separation value we also calculate the difference for multiple offsets. For example, if we difference every 5 frames we do that difference for all offsets from $M_1$ to $M_n$ with an increment of $\Delta M$. An example would be subtracting every 5 frames starting at frame 1 then subtracting every 5 frames starting at frame 2 and so on. Again, in general we want the option to subtract multiple offsets in increments of $\Delta M$ within a range of A to B. For example we may want to increment the offset 5 from 0 to 20. That would mean we do all the ranges of differenced frames starting at frame 0, then do them all again starting at frame 5 and so on.

Once we find the brightest pixels from all the calculations (both all offsets and all frame separations) we now know what pixel to look at, where the waveform starts and what the separation is of the peaks and valleys.

The next calibration we do is adapted to these values and we only calibrate based on those values.

For example, assume that we find that the peaks and valleys separation is every 25 frames and the starting point is 5. Now we know the waveform restarts every 50 frames. So if we recalibrate, it would be at position 55, 105, 155 . . . and so on. This eliminates the need to do all the calibrations above or what we call the initial calibration.

So in terms of the above, the Initial Calibration is the one that does all separations and all starting points. A recalibration (adapted from the initial calibration) uses the known values determined from an initial calibration. All of these operations are conducted by the processor in a substantially autonomous manner.

Example

Simple frame differencing example using 3×3 array:

Assume we are using a camera with 9 pixels in a three by three array operating at 10 frames per second.

We believe the signal of interest has a frequency about 0.1 Hz so max and min values will occur at a frequency of 0.2 Hz, meaning max and min values should be about 5 frames apart. We decide to conduct frame differencing tests at 4 frames and 5 frames. Each test will calculate 4 frame differences.

To test the 4 frame possibility, we select frames 1, 5, 9, 13 and 17 for frame differencing. To test the 5 frame possibility we select frames 1, 6, 11, 16 and 21 for frame differencing.

The frames have the following values:

| Frame | | | | | | | |
|---|---|---|---|---|---|---|---|
| Frame 1 | 3 | 3 | 5 | Frame Difference 1 | 0 | 0 | 5 |
| | 3 | 3 | 5 | | 0 | 1 | 5 |
| | 3 | 3 | 5 | | 0 | 0 | 5 |
| Frame 5 | 3 | 3 | 0 | Frame Difference 2 | 0 | 0 | 5 |
| | 3 | 2 | 0 | | 0 | 1 | 5 |
| | 3 | 3 | 0 | | 0 | 1 | 5 |
| Frame 9 | 3 | 3 | 5 | Frame Difference 3 | 0 | 0 | 5 |
| | 3 | 3 | 5 | | 0 | 1 | 5 |
| | 3 | 2 | 5 | | 0 | 1 | 5 |
| Frame 13 | 3 | 3 | 0 | Frame Difference 4 | 0 | 0 | 5 |
| | 3 | 2 | 0 | | 0 | 1 | 5 |
| | 3 | 3 | 0 | | 0 | 0 | 5 |
| Frame 17 | 3 | 3 | 5 | Total Frame Dif. | 0 | 0 | 20 |
| | 3 | 3 | 5 | | 0 | 4 | 20 |
| | 3 | 3 | 5 | | 0 | 2 | 20 |

In this test, pixels (1,3), (2,3), and (3,3) are selected as the largest pixels, each having a total time frame difference of 20 with a combined total of 20 for the three largest array values

| Frame | | | | | | | |
|---|---|---|---|---|---|---|---|
| Frame 1 | 3 | 3 | 4 | Frame Difference 1 | 0 | 0 | 4 |
| | 3 | 3 | 4 | | 0 | 1 | 4 |
| | 3 | 3 | 4 | | 0 | 0 | 0 |
| Frame 6 | 3 | 3 | 0 | Frame Difference 2 | 0 | 0 | 4 |
| | 3 | 2 | 0 | | 0 | 1 | 4 |
| | 3 | 3 | 0 | | 0 | 1 | 0 |
| Frame 11 | 3 | 3 | 4 | Frame Difference 3 | 0 | 0 | 4 |
| | 3 | 3 | 4 | | 0 | 1 | 4 |
| | 3 | 2 | 4 | | 0 | 1 | 0 |
| Frame 16 | 3 | 3 | 0 | Frame Difference 4 | 0 | 0 | 4 |
| | 3 | 2 | 0 | | 0 | 1 | 4 |
| | 3 | 3 | 0 | | 0 | 0 | 0 |
| Frame 21 | 3 | 3 | 4 | Total Frame Dif. | 0 | 0 | 16 |
| | 3 | 3 | 4 | | 0 | 4 | 16 |
| | 3 | 3 | 4 | | 0 | 2 | 0 |

In this test for five frames, pixels (1,3), (2,2), and (2,3) are selected as having the largest values (16, 4 and 16, respectively) but the total combined value of the three pixels is only 36 as compared to 60 in the test for four time frames. So this test would indicate that a four frame difference is the best time interval and the pixels to be monitored would be 1,3 and 2,3 and 3,3. However, similar test will be run for other phases for both the four and five frame intervals. In the next test, the four frame interval will use frames 2, 6, 10, 14 and 18 and the five frame test will use frames 2, 7, 12, 17 and 22. These further tests are changing the phase of the test. Assuming the next tests produce results that have lower total than 60, the first four frame test will prevail and its "brightest" pixel locations will be chosen for monitoring.

Applicants have also tested the invention, and found that it performs well, even with asymmetric periodic waveforms. Three examples using skewed or asymmetric periodic waveforms: SawtoothRight, SawtoothLeft, and LubdubRight were evaluated as described more fully in Applicant's co-pending application, Ser. No. 14/757,259 "Method of adaptive array comparison for the detection and characterization of periodic motion", U.S. Publication No. 2016/0217588. Each of these three waveforms incorporates a skewed 30-frame peak-to-peak periodicity evident. SawtoothRight and SawtoothLeft waveforms have a 2:1 skewed rate of falling compared with rising measurement values. LubdubRight also contains a second peak in each periodic cycle. The inventive method was able to accommodate the features of these waveforms without difficulty.

Comparison of the invention with traditional "frame difference" methods.

It will be understood that although the invention involves subtracting pixel values at one time from those at another time, the inventive Adaptive Array Comparison method differs considerably from traditional techniques broadly referred to as "frame difference" methods in at least the following ways:

1. Adaptive Array Comparison specifically targets individual frames at particular references for the purpose of exploiting periodic signals.
2. Adaptive Array Comparison adapts to the signal, learns from the signal and modifies its approach.
3. Adaptive Array Comparison targets periodic signals to isolate them from the background.
4. Adaptive Array Comparison relates to time intervals based on signal of interest.
5. Adaptive Array Comparison isolates particular phases of motions, max and mins in its approach.
6. Adaptive Array Comparison is an iterative process and involves comparison of the results of those iterative steps.
7. Adaptive Array Comparison is a temporally based and links arrays to particular points in time.
8. Adaptive Array Comparison generally involves multiple comparison of arrays over time and relies on the cumulative result.

The user interface may be configured in a wide variety of ways, as described more fully in the following examples.

Example

Figure 15A:
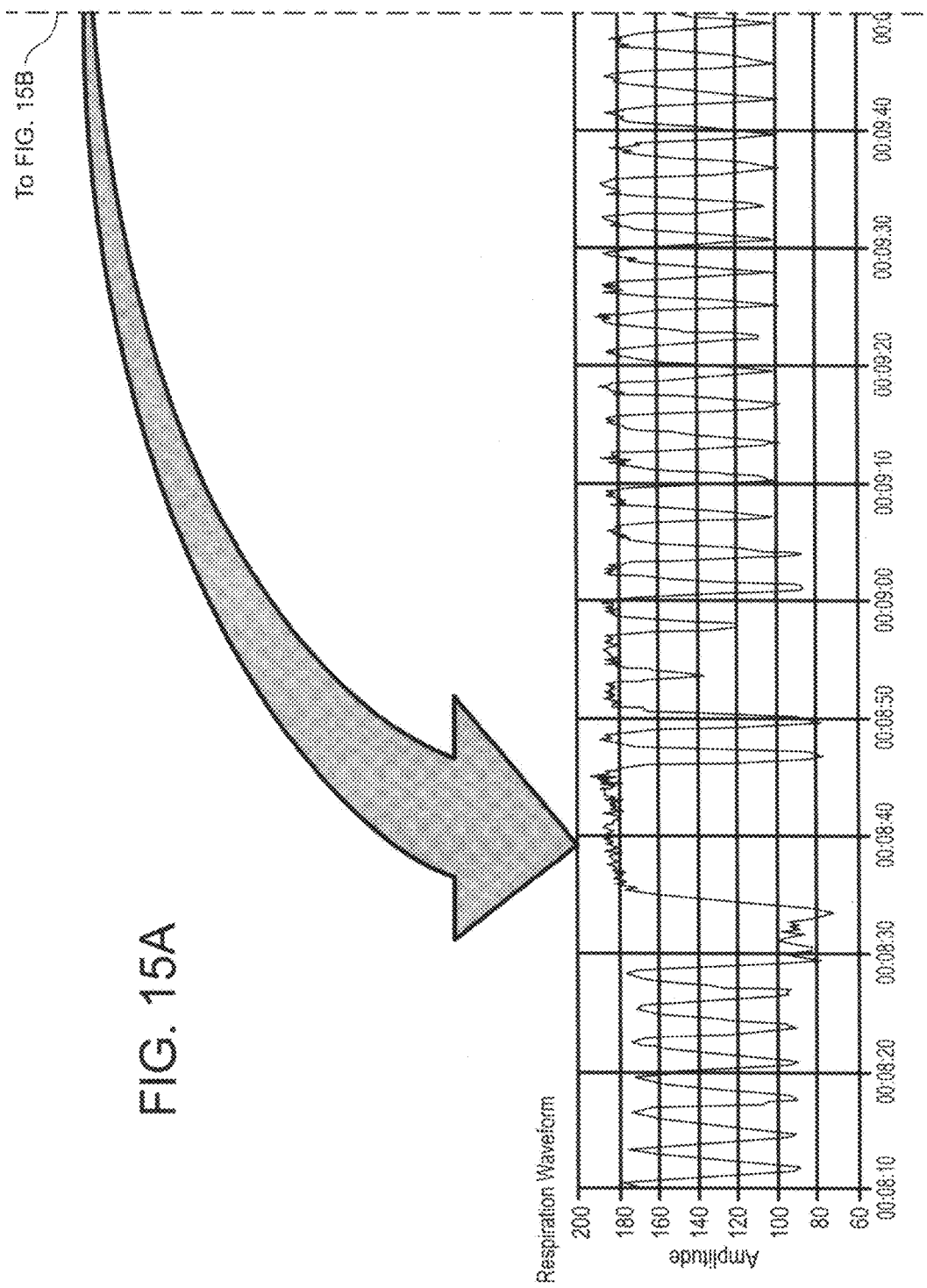
FIG. 15 illustrates the ability of a user to rewind the acquired data files (indicated conceptually by the large arrow) to return to a point in time at which an event occurred.
Figure 15B:
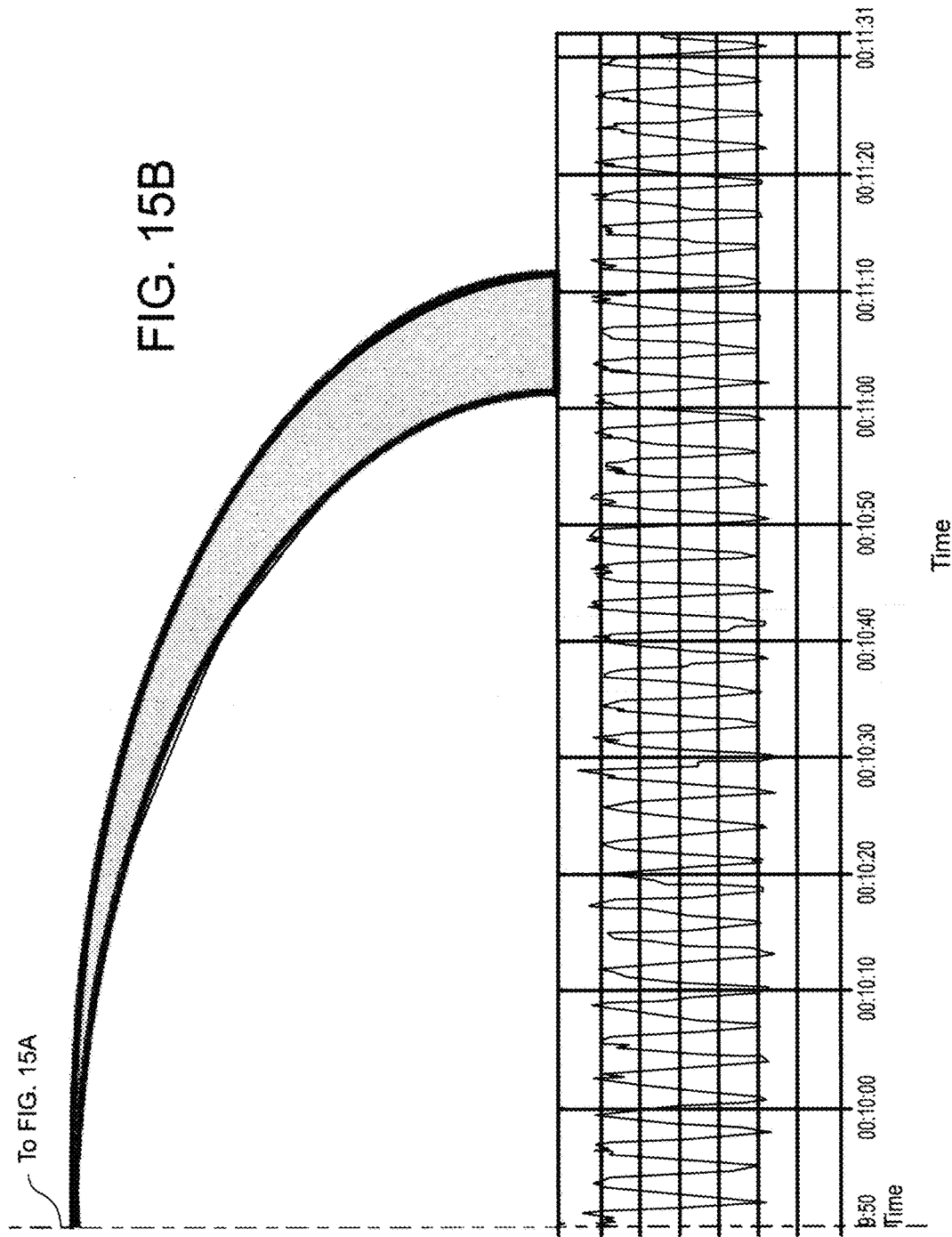

Because the data may be stored with the raw video on a common time basis, if an alarms sounds and everything appears to be normal, the user may simply rewind the video to review more closely what caused the irregularity, as shown in FIG. 15 for the related problem of respiration monitoring. The information, in the present case, might include the video, motion waveform, and a condition or quality index derived from "standard" or historical data. So the user might press a button that rewinds the waveforms and video or goes back a preselected amount of time or to a specific preselected time and plays back the waveform and video side by side to show what triggered an event or an alarm condition, thus providing a more complete understanding of the event. Because the video is time stamped, the event of interest may be correlated with factors such as power surges or dips, lightning, temperature excursions or other environmental conditions, etc. Thus, the invention allows a more holistic awareness of the situation and makes predictive maintenance correspondingly more useful and robust.

Example

Using Waveform Signatures to Detect Events. FIG. 13A shows a healthy waveform and FIG. 13B shows an irregular one, again taken from respiration data. An event is clearly seen in the middle of the irregular one. Here this event will be categorized, stored, indexed and/or reported and may contribute to the condition index.

Templates may be prepared to help the user correlate an event to some known conditions. For example a set of templates may exist including a baseline waveform for a newly-installed motor or pump of a particular model and later measurements are correlated against that template to define changes, quantify wear and tear, and inform the maintenance decision-making process. The information may also be uploaded to a central database and/or provided to the maintenance professional. The information may also be included in a report. Exemplary templates may include, but are not limited to, a new machine, a worn bearing, a loose coupling, or a machine nearing its end of life.

Events may be indexed and a single frame or video clip may be extracted that corresponded to the same time. Those compilations may be stored. One index may be targeted in particular, for example, events associated with power quality. The user may review those events to determine if an investment in power conditioning may be helpful to improve equipment life and performance.

Events may be correlated with timing through the day/night and the same procedure as described above would allow the user to determine if particular times of day/night are correlated with better or worse equipment stability.

It will be appreciated that the user interface may take a variety of forms, and in particular, the invention may be implemented in a mobile application, so that, for example, a service technician can view the data acquired at a work site and make a decision about whether a maintenance call is urgent or can be scheduled later. The technician may further have access to a database (onboard the device or on a remote server) to assist the evaluation process. The database may include historical or baseline data for a particular machine being examined, and may also include comparable data for similar machines previously examined in other locations. The technician may also upload new information to the database for later analysis and comparison.

Example

Figure 16:
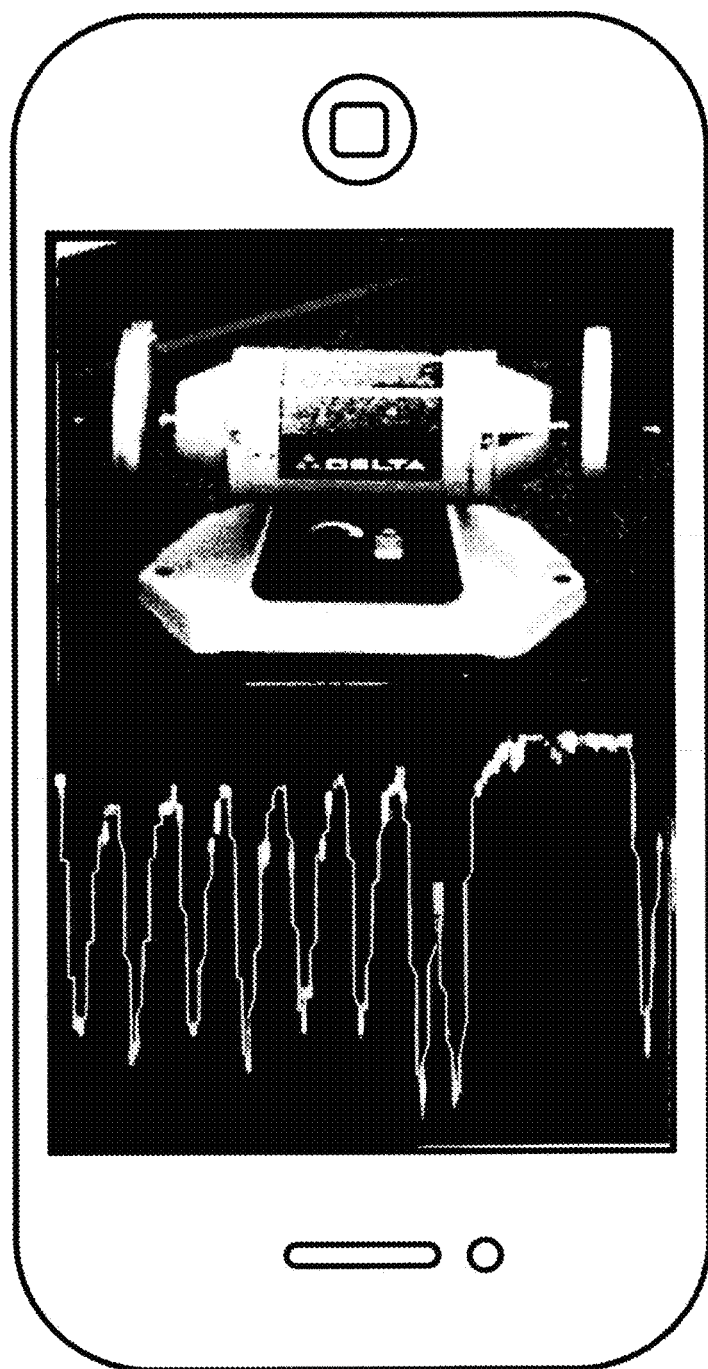
FIG. 16 illustrates an example of a user interface implemented for mobile devices according to another aspect of the invention.

FIG. 16 shows a conceptual image of a potential graphical user interface (GUI) showing a vibration waveform and video in real-time from a camera where the vibration waveform would be derived from the video. This type of interface would allow the user to view the data using a smart phone.

The camera does not have to be placed right next to the equipment. Applicant has discovered through experimentation that the inventive process is sufficiently robust that reliable data can be collected from an object in a random position in the frame and surrounded by various items, which may be stationary or might be moving to some degree. Another important advantage of the invention is that the measurement itself is not invasive or disruptive. It requires no contact with the equipment or process and no tap into the equipment's power feed.

Example

Ability to Track More than One Waveform. Conventional standoff and contact methods cannot test more than one machine at a time. The ability to do so would clearly be valuable for the typical plant environment where many different components may be located in close quarters and may each be vibrating independently.

Applicants have experimentally demonstrated that, for example, a mother and child co-sleeping were simultaneously detected, with the invention capturing dual waveforms from the same video image and displaying both waveforms simultaneously, as described and illustrated in Applicant's co-pending application Ser. No. 14/757,256, "Method of analyzing, displaying, organizing, and responding to vital signals", U.S. Publication No. 2016/0210747. It will be appreciated that the same approach may be extended to the factory environment.

It will be clear to the skilled artisan that the invention can be used in a factory to monitor two machines simultaneously in separate cells, in a refinery to monitor multiple valves or pumps, etc. The information may be uploaded to the cloud or to a server for continuous monitoring or, for example, to a maintenance department or field service team.

Using a normal cellphone or mobile device, the application could produce fast results for a quick assessment of a situation or to prioritize various potential maintenance jobs. Applicants have demonstrated that currently-available mobile devices have sufficient computing power to do this. The method is currently running successfully on an ARM11 Raspberry Pi board, which is slower than the current iPhones and likely the 5s too. An early prototype ran successfully on the iPhone 5s using its internal camera.

Example

The invention may be configured to run on a mobile device such as a smart phone or tablet computer having a built-in camera. A user could carry the device from one area to the next, collecting video and running the analysis for many machines or process points in a plant environment. The user may acquire the video such that the image includes a fixed object or fiducial not connected to the vibrating component, thereby correcting for any shaking or instability in the handheld camera.

The video file and analysis could be stored in the mobile device or uploaded to a central server or database. At the same time, the mobile device might download other data from the server, such as historical data collected from the same machine or comparative data collected from similar machines.

Although in many Examples, it is contemplated that the video image is focused on a particular machine or component under examination, it will be appreciated that the invention may equally well be carried out in a reversed configuration in which the video camera is rigidly mounted on the equipment or component and is focused on a convenient stationary object in the environment. The fixed object might be a column or other structural feature of the building, a poster or plaque affixed to a nearby wall, etc. In such a configuration, the apparent motion of the fixed object will mimic the motion of the camera on the vibrating component and the video file may be analyzed in a completely analogous manner as described earlier.

Multiple Region Perimeter Tracking and Monitoring

A perimeter-tracking approach may be used to prevent an unknown factor from entering the monitoring space of the individual machine or simply a general area. This can also be used for objects exiting the area. The user will be able to create a perimeter (via a user interface) around the area that he/she wants to monitor and does not want any intrusion into.

Multiple methods of motion detection can be used in the perimeters. For example, a technique such as adaptive array comparison can be used to see if changes have occurred around the perimeter from one frame of the video to the next.

Another technique may be comparison of frame intensity values in the area of interest. Regions can be selected and those regions summed for a total intensity level. If that intensity level changes frame to frame by a certain threshold, motion is determined to have occurred.

Blob comparison may also be used for motion detection.

Single pixel edge motion may be used. It will be possible to determine the perimeter with great accuracy based on movement of an edge of a single pixel or virtual pixel, which will allow for a much greater degree of accuracy compared to using conventional blob techniques. The area being selected does not have to be a series of large boxes as in current technology but instead can be any sort of perimeter that the user chooses to select. This could offer the ability to use a very narrow single pixel perimeter or single virtual pixel comprised of multiple pixels.

Feature tracking may be used by locating features in the perimeter and tracking their location in the perimeter. If their centroid location changes then motion is detected. Correlation of a selected number of pixels with a feature in them can be correlated to sub-regions in successive frames to determine if the highest correlation of the original set of pixels is correlated more highly to another location other than the original location.

It will be understood that there are several factors that could create false readings, including but not limited to outside factors such as wind from the outdoors, vibration from another device in the room, movement of a curtain or other object in the room, or latent movement from someone near the subject. To help factor out these false positive readings Applicants contemplate the use of various techniques to isolate targets of interest.

Example

The invention may be installed and used in conditions where there are multiple regions to isolate, such as a busy production line involving numerous work cells, individual robots, etc. Each area can have separate perimeter monitoring using perimeters drawn by the user via the GUI.

Isolation of Frequency:

Applicants have also recognized that the invention may further use frequency isolation and a learning algorithm to learn the likely machine vibration rate and distinguish it from outside factors that could produce a vibration or movement in the field of view of the camera. This will help distinguish movements in the field of view (such as a fan or wind blowing a curtain) from movements associated with vibrations of interest.

Motion may be allowed inside the area of interest without alerting or affecting the monitoring of the perimeters. This would allow for an object to freely move within the area of interest, for example a welding robot, but still allow for monitoring of the perimeters.

An object detected moving in the perimeter can be characterized by the number of regions in which its motion is detected to give an estimate of size. The time between detections in various blocks can give information as to speed based on the known physical projection in space of each pixel. The series of blocks through which the object is detected to be moving can indicate the direction of travel.

Motion can be detected through the inventive method of array comparison of different frames. Frequencies such as fast moving objects can be filtered out by comparing frames with larger separation in time, and slower frequencies or a slower moving object can be filtered out by comparing frames with shorter separations in time. Thus, the invention can be used to isolate certain motions for detection or rejection.

Using light level changes to detect motion can cause false a positive indication of motion from things that change the illumination of the scene but are not objects moving in the field, such as fans or curtains moving from air flow. Comparing different separations in frames (hence different separations in time) can eliminate these spurious indications. For example, the slow light level changes from the natural daylight cycle would not be detected if a short time separation in frames are compared.

The invention may further include a method for determining, comparing, measuring and displaying phase, which is of particular relevance for the case of machinery.

It has been shown that intensity changes over time can be detected and correlated to physical phenomena. In many cases those signals may appear to be periodic. The periodicity can be described by frequency, amplitude and phase. In addition to the frequency and amplitude, phase is an important characteristic of the periodicity that helps temporally describe the signal and also describe one signal relative to another and relate those signals to patterns of repetitive events such as periodic motion.

The following example describes a method for extracting and analyzing phase information from time varying signals. This may be done on a single pixel level and/or for a plurality of pixels. The phase information is shown and displayed in numerous ways. Information can be gathered from the time varying signal based on the phase and its relationship to other parameters.

Example

Simplified Explicit Stepwise Procedure

1. A time varying signal is sampled in time with a photo detector, transducer or other suitable device. This sampling represents a time sequence with appropriate resolution to correctly sample the signal of interest.
2. Multiple samples can be collected simultaneously with a plurality of pixels, e.g., with a video camera where every pixel in a single frame represents a sampling at the same point in time at different spatial locations in the scene.
3. The resulting sequence is an array of X×Y×t where X represents a spatial dimension, Y a spatial dimension orthogonal to X, and t represents time.
4. FFTs are performed in the time domain along the t axis for every pixel or element in the array. The FFT then returns a frequency spectrum for each pixel along with the amplitude and phase for each frequency.
5. The phase information for each frequency can be displayed. For a given frequency, a phase reference such as 0° may be arbitrarily selected or may be associated with trigger, pulse, absolute reference, specific sample, or frame as may be preferred or selected.
6. To create a phase mask image we plot a representation of phase for a given frequency in the same pixel from which it was measured. To create a two dimensional image we first set the frequency we are interested in. For example, we may want to see the phase relationship for the 30 Hz signal. To do this we filter the image so that pixels that are in the selected phase range are white (represented numerically as 1) whereas all others are black (represented numerically as 0). The phase range may vary but for this example we will use ±5°. For example, if we select 30 Hz and 55° then the image will show white (or 1 numerically) where a signal exists that has a frequency of 30 Hz and has a phase from 50°-60°. This has the benefit of showing all elements of the scene that are in phase at the same frequency as they all appear white while the rest are black.
7. Taking this a step further, one can hold the frequency constant while adjusting the phase to 235° which is 180° out of phase of 55°. In mechanical systems, misalignment is typically 180° out of phase across a coupling. In this manner it is possible to look at two different phase values to see if there is a phase shift indicative of misalignment. Another example would be to look at a structure such as a bridge to see if structural elements are moving in or out of phase.
8. Now if one were to start at 0° and toggle to 360° one would see all the different locations of the different phases for the 30 Hz signal. They would be indicated by the fact that the pixel turns white.
9. This entire process can be repeated for every frequency.

Figure 17:
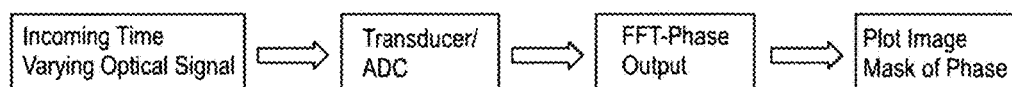
FIG. 17 illustrates the steps in one approach for determining and displaying phase according to one aspect of the invention.

FIG. 17 outlines one approach for computing and displaying phase.

It is possible to use intensity readings to increase the information in the phase images. For example, one could take the intensity of the frequency at each pixel and multiply it by the phase mask image. Since the phase mask image is binary (if the signal is at a particular phase it is white, or valued 1, and if it is not at the selected phase it is black, or 0) the phase image acts as an image mask that will only allow the intensity values to pass if it is at the selected phase. All others will be zero. If it is in phase the intensity is preserved since it is multiplied by 1. This will create a scaled image that shows only things at a given phase and what those intensities are.

Example

Use of phase imaging is illustrated in FIG. 18.

Figure 18A:
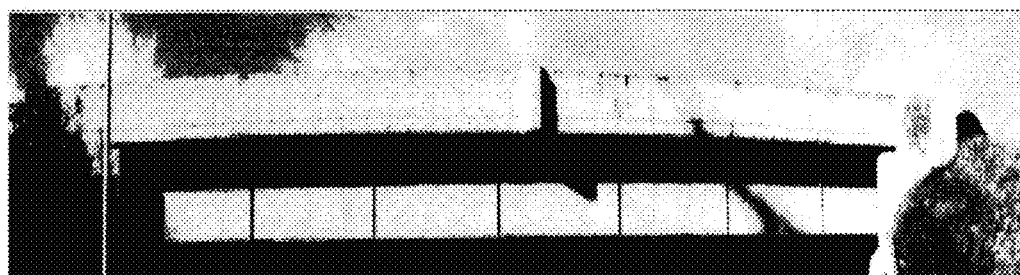
FIGS. 18A-C, illustrate the use of phase information to analyze vibrations in a bridge.

FIG. 18A shows a single image from a video sequence of a bridge. During this sequence a vehicle passed over the bridge (not shown).

Figure 18B:
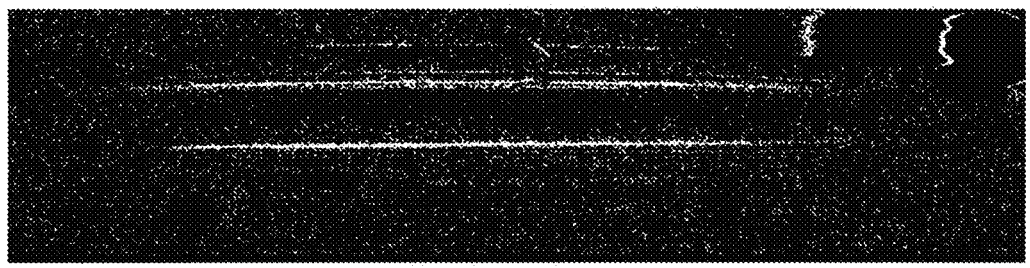

FIG. 18B shows a single phase mask image depicting a single phase (that of the fundamental vibration of the bridge) at 2.25 Hz, the bridge fundamental frequency. In this image things moving in phase show up as white (value 1) whereas things that are out of phase show as black (value 0). The image is scaled such that 0 is black and 1 white. One can see that the motion on the I-beam support shows a clear feature of motion indicating the entire span is moving in phase with itself, as one would expect.

Figure 18C:
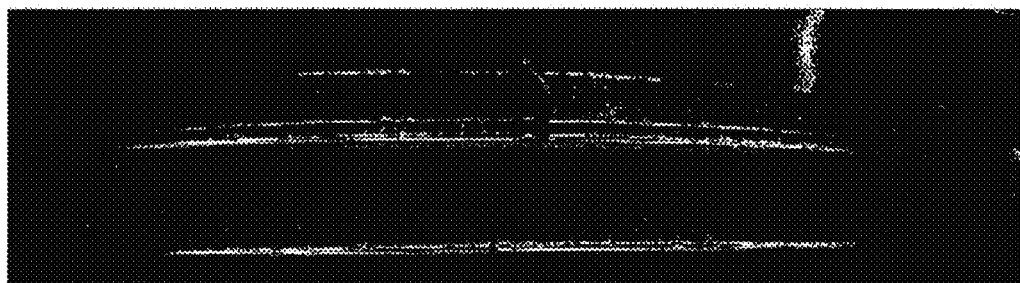

FIG. 18C shows an image of the phase mask seen in FIG. 18B multiplied by the intensity at each pixel of the amplitude of the 2.25 Hz signal, which relates to motion. One can see that now the phase image is scaled with relative values. Furthermore the image is much cleaner as small amplitudes of frequencies can be set below a threshold using the noise reduction technique.

If the amplitude of the frequency of interest due to intensity changes is calibrated to a particular value then the phase mask image (that is composed of 1s or 0s denoting in or out of phase respectively) can be multiplied towards a calibrated frequency amplitude image or array. Then the resulting image displays only things in phase at a particular phase of interest at a given frequency and offers a calibrated value. That calibrated value may be from anything that is causing the signal levels to change. It could be temperature variation from thermal IR imagers, displacement from moving features in a visible image or even variations in absorption levels through a transmitted medium.

For a measurement made with video imagery the phase may be referenced simply to the first image taken so that all phase readings are relative to the first image. However it is possible to synchronize the phase readings to another signal. This could be a trigger pulse or even a time varying optical signal in the scene of the imager.

Exposure modes on imaging sensors are often different. Two types of modes are global and rolling shutters. Global shutters expose every pixel at the same time. Rolling shutters expose lines of the sensor at different times. In the case of a global shutter all pixels are exposed simultaneously so the phase relationship is preserved across the sensor. In the case of a rolling shutter there are variations in the timing of exposure from pixel to pixel. It is possible to realign temporal signals based on the known delay between pixels after they are read from the imaging sensor. By accounting for this offset we can preserve the relationship of phase across all pixels.

It is possible to use the phase information in a noise reduction manner. For example, in the event of a phase image mask where the array or image is binary (1s for in phase, 0s for out of phase) one can reject all pixels out of phase at a given frequency and given phase. When exploring an image, if many pixels effectively "turn off", it eliminates much background noise in the scene and makes detection much easier. This may be advantageous, for example, in a cluttered field or where many time-varying signals exist. Additionally, one can reduce noise by multiplying the phase mask image by the frequency intensity image and setting an intensity threshold below which the pixel is set to 0 or not represented in the scaling.

Mechanical or anelastic properties that have particular phase properties can be imaged and detected with the described technique. Phase relationship information can be exploited with the described technique to reveal physical parameters or other properties.

By cycling through all the phase mask images at a given frequency, traveling waves may be seen in the sequence of images created.

Different areas of the array or frame of the same or different phase mask images may be compared to show certain areas of interest indicating anomalies, e.g., one area that is out of phase with the rest. Or, these areas could be compared to find patterns indicative of physical phenomenon.

The following exemplary cases demonstrate some useful applications of this aspect of the present invention.

One use of phase presentation as described herein is to determine and to graphically display absolute or relative timing characteristics and patterns.

A second example is to demonstrate a modulation or a beat frequency or other characteristic which may correspond with a movement or other of an object of interest.

A third example is to represent a leading or a lagging event sequence made evident mathematically or graphically using techniques described herein. Again, this leading or lagging event sequence may be related to a movement sequence of an object of interest.

A fourth example of the present invention is to characterize highly repetitive displacement patterns such as a static or a dynamic constructive and destructive interference pattern resulting from multiple vibration wave fronts. The multiple fronts each typically originate from a point, line, or area of reflection, or originate from a point, line, or area vibration energy source. This technique may be used to discern false or positive indications. For example, a false indication may be found from a highly repetitive pattern which is more likely produced by a machine than a living being.

Method of Motion Amplification

Another method that can be used to further enhance the inventive technique is to amplify motion by an amplification factor. This factor determines the strength of the overlay of the difference image sequence on top of a static image from the original motion sequence. For example, if the factor is 1 there may be equal weight applied, whereas if the amplification factor is 30 the difference frames are increased in intensity by some factor relating to 30 in the composite image. This would allow one to determine how much of the difference sequence is present and how much the static frame is present. A factor of 0 may turn off the motion and just show the static image.

Example

Figure 6:
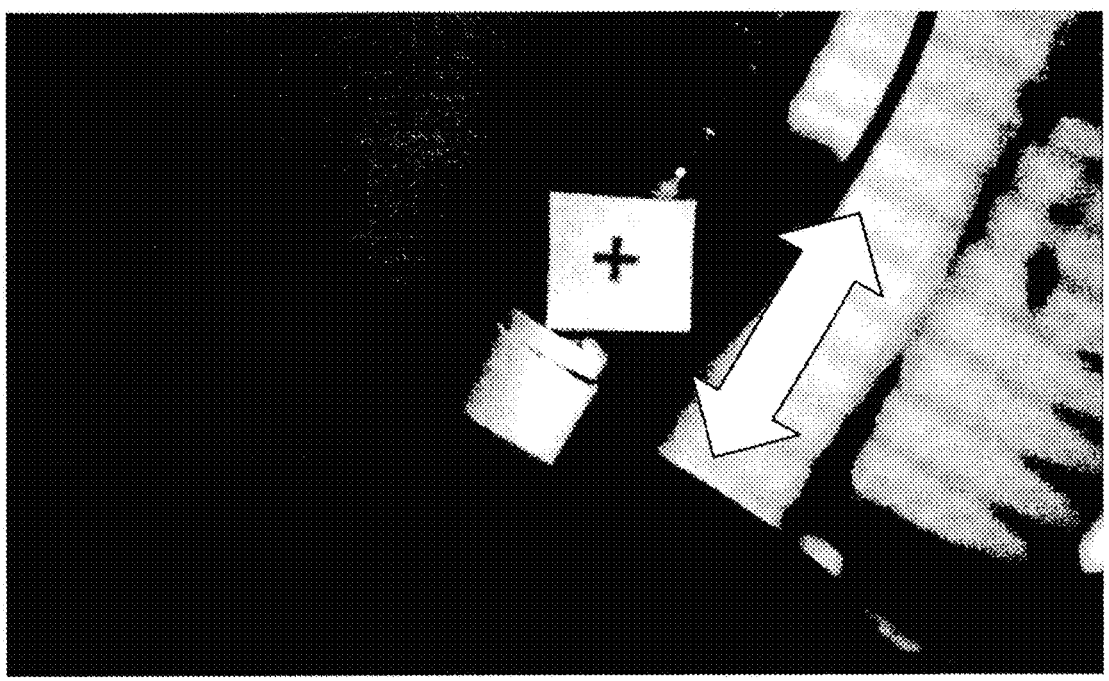
FIG. 6 illustrates a video frame in which a small paper square having a "+" shaped fiducial mark has been attached to a speaker, which is vibrating periodically in the direction indicated by the white arrow.

FIG. 6 shows the original image frame of a paper square with a plus sign, attached to a speaker vibrating periodically. The arrow in FIG. 6 shows the motion of the paper relative to the frame imaged by the camera. This image corresponds to what is being imaged in FIGS. 7 through 12.

Figure 7:
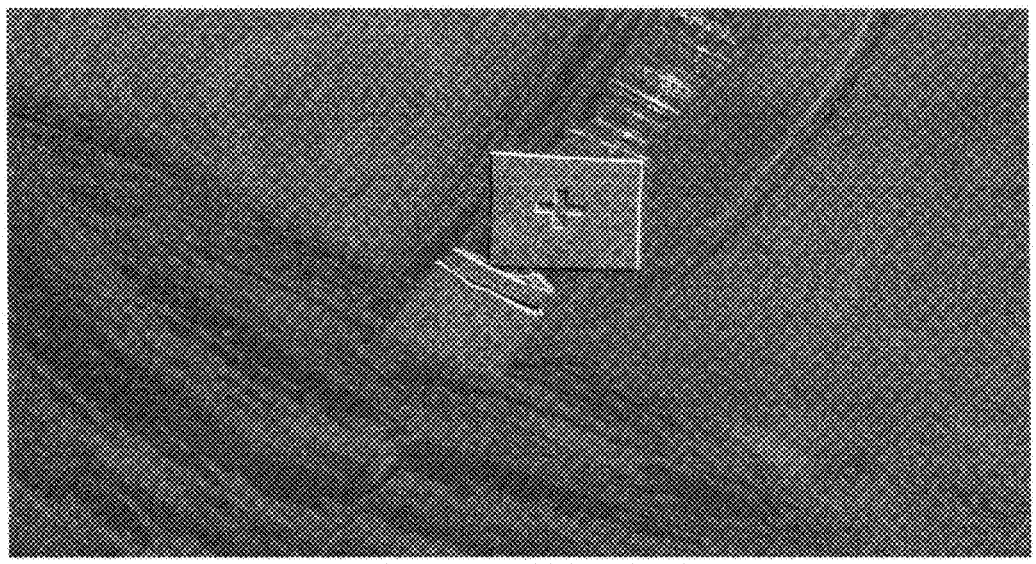
FIG. 7 illustrates a difference image, in which the bright lines on the edges of the paper indicate motion.

FIG. 7 shows a difference image in a sequence from the median reference frame. Notice the increased intensity change on the top and right side of the paper with the plus sign.

Figure 8:
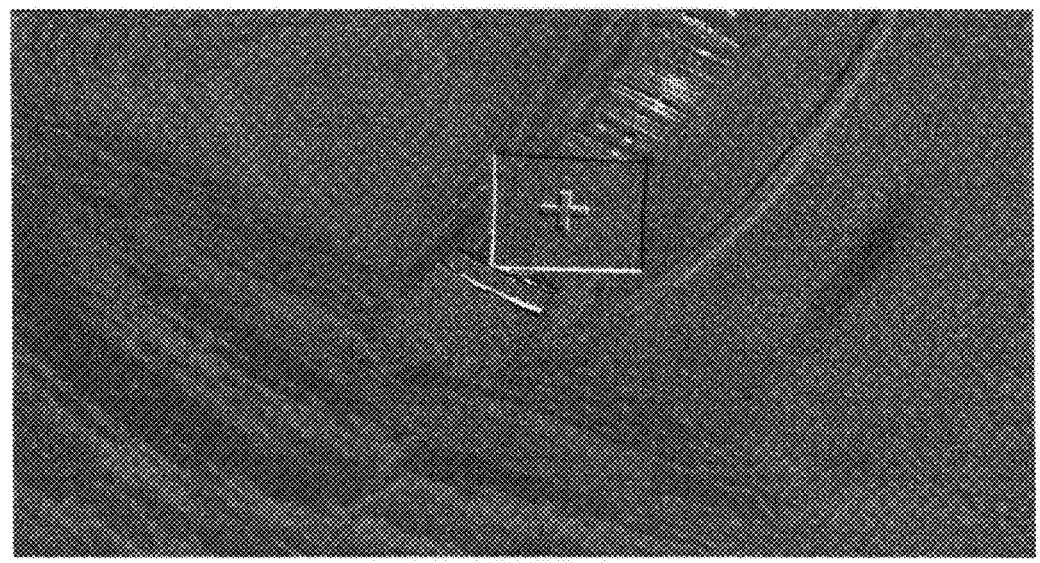
FIG. 8 illustrates another frame in the same sequence as FIG. 7, but in this instance the motion is in the opposite direction so the bright lines are orthogonal to those in FIG. 7.
Figure 9:
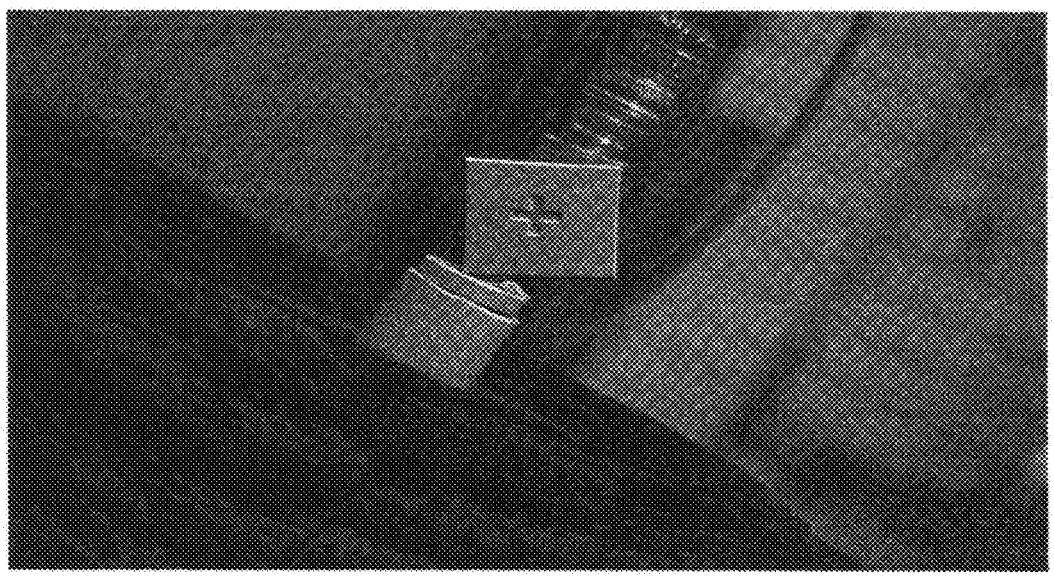
FIG. 9 illustrates the result when an amplification factor is applied to the difference image of FIG. 7, which is then overlaid onto the original image.
Figure 10:
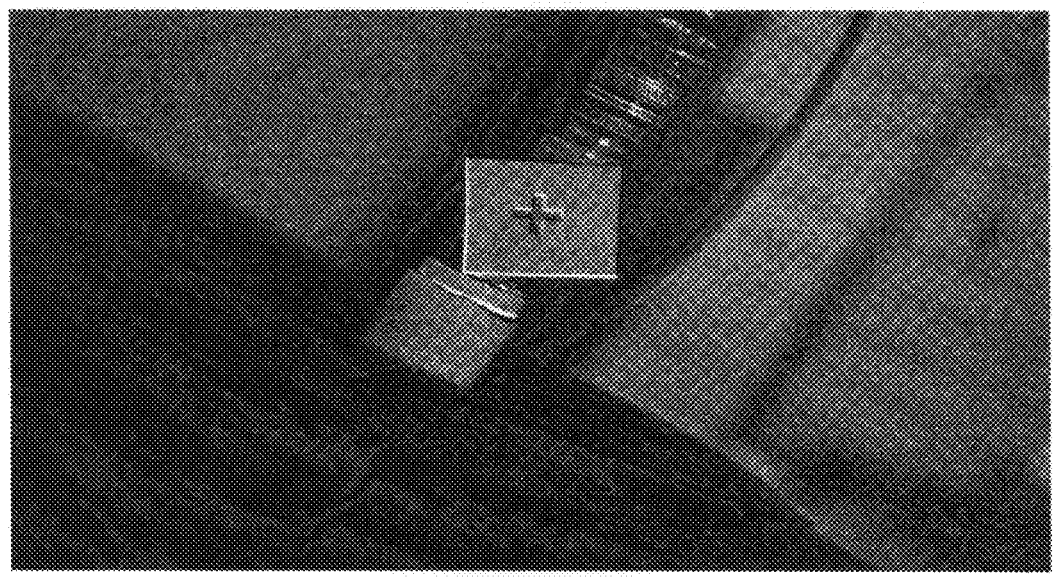
FIG. 10 illustrates the result when an amplification factor is applied to the difference image of FIG. 8, which is then overlaid onto the original image.
Figure 11:
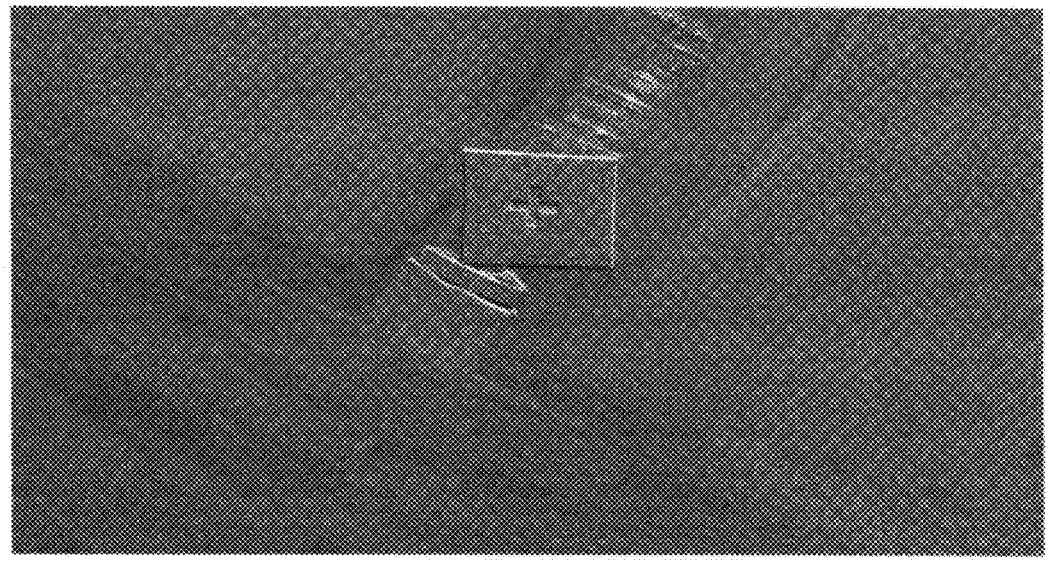
FIG. 11 illustrates a difference frame calculated using the mean frame rather than the median frame as the reference frame.
Figure 12:
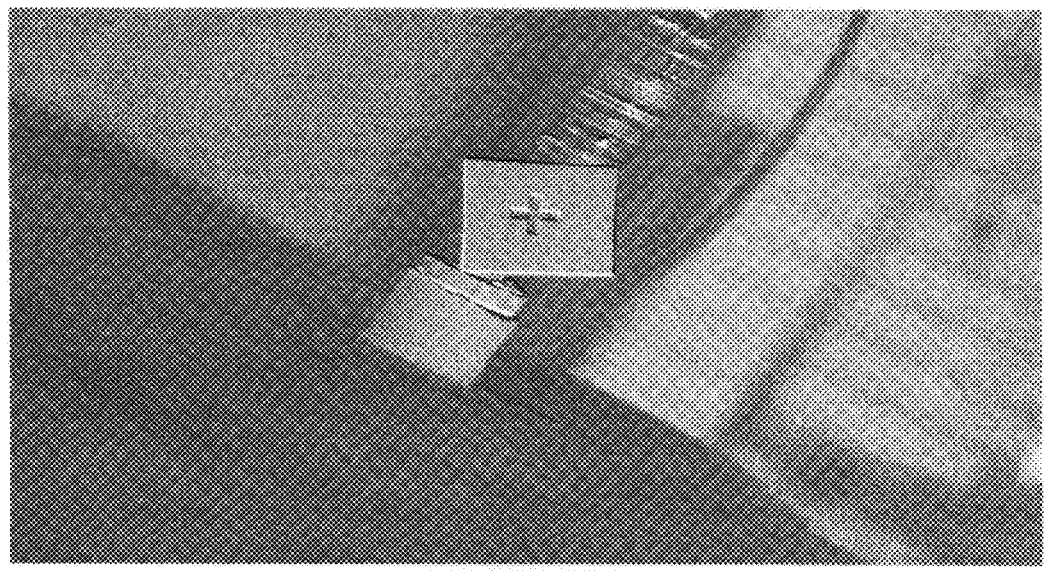
FIG. 12 illustrates a difference frame calculated using a single frame from the original video file as the reference frame (i.e., the reference frame was neither a mean frame nor a median frame).

One can see that in FIG. 8 the increased intensity change is now on the lower and left side of the paper. This is from a frame in the same sequence at a later timestamp. Comparing FIGS. 7 and 8 indicates the motion is up and to the right and then down and to the left. FIGS. 9 and 10 show the same behavior except that amplification has been applied to these frames, meaning there is an overlay to the original images such as the one shown in FIG. 6. The amplification factor determines the relative contribution of the original image such as FIG. 6 and the difference portion such as in FIGS. 7 and 8. More of the spatial detail of the scene is present in FIGS. 9-10 because overlay of the original image in the original sequence contributes to the image displayed. FIGS. 11-12 illustrate similar results using difference frames calculated using reference frames other than the median frame.

The following explanation will further illustrate the conceptual basis for the inventive motion amplification process:

Example

Amplification works by amplifying the changes in the images that are associated with motion. Often an edge or feature in an image is not ideal, i.e., the threshold or contrast change does not fall on one pixel. Although we present a non-ideal case, amplification would work equally well in an idealized scenario. This would be the case of a larger pixel or high quality optics to put the edge solely on one pixel.

Figure 20A:
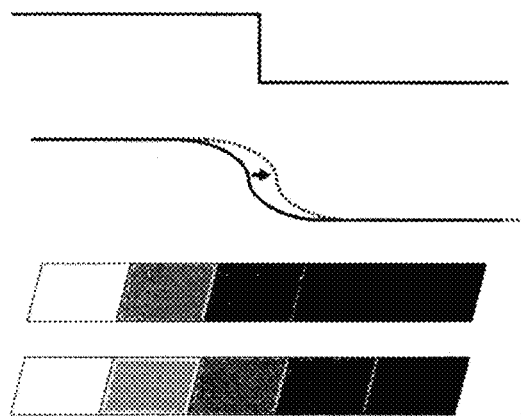
FIGS. 20A-C illustrate the conceptual basis for motion amplification.

FIG. 20A shows an idealized edge at the top, transitioning from a high to low value left to right. The center solid line shows the non-idealized case, more commonly occurring due to irregularities at the surface of the target, degraded image quality from optics or variations resulting from a turbulent light path, to name a few. Also shown in the center is a dotted line indicating the motion of the edge feature moving to the right.

At the bottom of the figure are two rows of pixels showing the intensities of the pixels from imaging the edge. The top row of pixels shows intensities of the edge before it moves while the bottom row shows intensities after it moves. Note the overall brightening of the three center pixels as these portions of the image are imaging the edge detecting variations associated with it moving. Also note the left and right most pixels don't seem to change as they are not imaging the edge.

FIG. 20B again shows the motion of the edge towards the right of the image. Again we see the before and after effect on the pixels in the top two rows of pixels. The bottom row of pixels shows the numerical change associated with each pixel as the edge moves right. This is the difference value of those pixels. This value is the value that gets amplified. For example if we amplify these values by a factor of 10, the +2 becomes 20, the +10 becomes 200, etc.

Figure 20B:
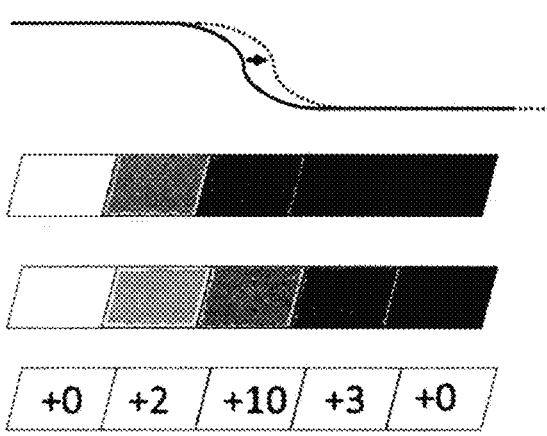
Figure 20C:
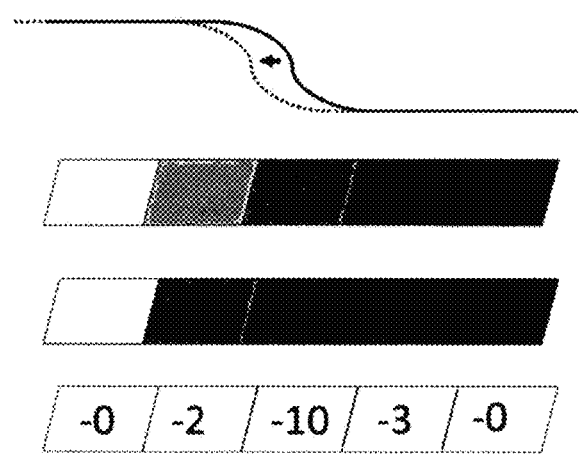

FIG. 20C shows the same effect as FIG. 20B except the motion is now to the right and more of the dark side of the edge is imaged. Note the pixel intensities darken where portions of the edge are imaged and the values in the bottom portion of the figure denote the integer values of pixel changes decreasing.

These amplified differences are then used to create the amplified motion sequence. Note we may add these amplified sequences to the original video sequence to increase the effect of seeing what was in the scene before amplification or we may choose to visualize only the amplification sequence.

Applicant has discovered that this method can be further modified to create the appearance of exaggerated movement in the image, by superimposing the differenced frame onto the reference frame and using the resulting image to replace the original frame in the video.

Example

The first step is to choose a reference frame. In the case of periodic signals the median works best because that is the zero value. (The median image is created by calculating the median value of each pixel over the length of the video and using all those values to create a median image.) Then every frame is compared to that reference frame to create and new set of differenced images. If the video clip is 800 images long (10 seconds at 80 fps) this will comprise 800 difference frames. These images will likely show relatively small variations in pixel intensity because that is only what has changed.

The next step is to amplify. For example, if we want a factor of 30 amplification we multiply all the differenced frames by 30, so if one particular pixel in a difference frame has value 2 it becomes 60. This creates a new set of differenced frames that are amplified by the selected factor.

Figure 19A:
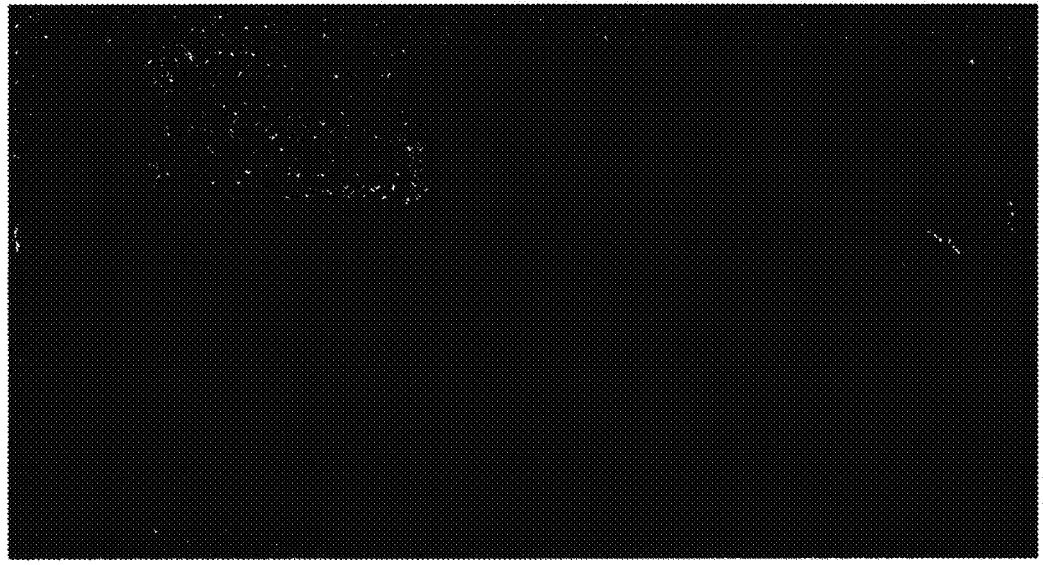
FIGS. 19A-B illustrate the use of motion amplification to visually exaggerate the apparent movement of an object.
Figure 19B:
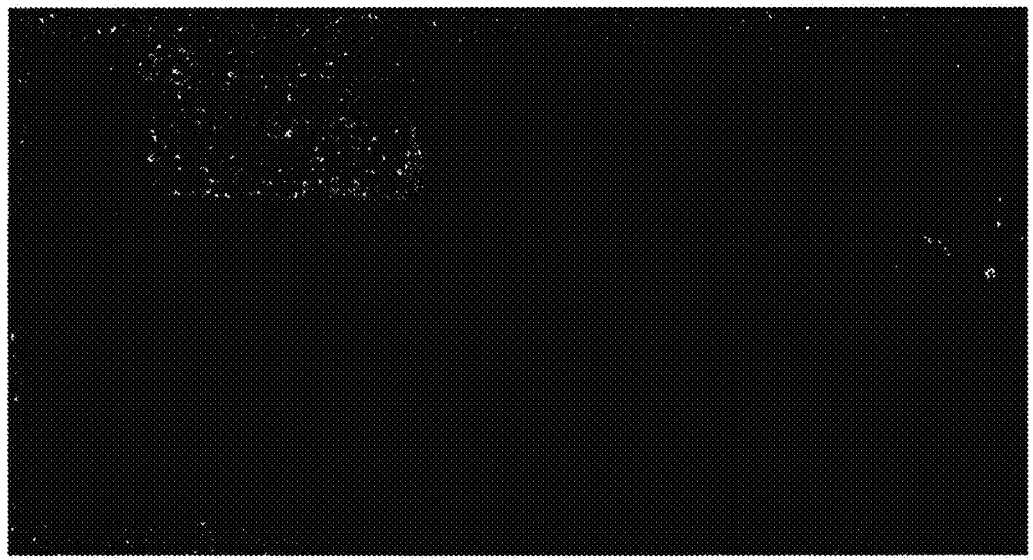

Those amplified difference frames are now directly added to the original frame. This helps to introduce a semblance of the original scene and give a baseline. (Note that 8-bit images are only 0-255 so because we added to the original image we may need to rescale to make sure the intensities fit in 8 bits. This will introduce a small amount of noise into the image, as seen in FIGS. 19A and 19B, but does not interfere with the added functionality of being able to clearly visualize the motions.)

Now we have a new set of images that comprise the original image plus the amplified difference frames that represent motion. These new frames are put back in the video and played back. The frame rate is generally reduced so the motions are easier to see, especially if the motions occur at high speed.

Example

A short video was taken of a small electric motor coupled to a supported rotating shaft having a flywheel centered between the supports. In the raw video, some eccentric motion can be seen in the coupling between the motor and the driven shaft, but the motor itself appears to be motionless. However, after applying the motion amplification procedure described above, the movements become clearly visible so that one can see exactly how the motor is moving or rocking during operation. Careful examination of two still images, FIG. 19, shows a visible difference, with the apparent position of the motor slightly more parallel to the ROI box in FIG. 19A, and more skewed in FIG. 19B.

When viewed as a video, the visual result is not only striking, but in many ways completely surprising, as there are no additional steps or mathematical modifications to cause the apparent motions to be amplified. The process is actually targeting motions that are subpixel, in many cases much less than a pixel. The process for creating the amplified motion video simply alters the individual pixel, in other words a measurement from one pixel isn't directly altered or translated to a neighboring pixel to make it look like the edge moves into that pixel. In most cases, defocusing and other issues often cause the light in about 4 pixels to be changed by an edge motion so each one of those respective pixels' motion is amplified and causes the motion effect to be present in all of them.

Applicant speculates that one phenomenon that might be at work here is that multiple pixels are behaving in a correlated way. In other words, when an edge or feature moves one sees the effect of motion in multiple areas and visually processes that as motion. For example with the rocking of the motor, one sees the entire side of the motor go up, so all of those pixels are working together in a correlated way to make the viewer perceive that the object is moving.

Applicants note that although the motion amplification process has been descried with particular reference to periodic movements, the principle may equally well be used to amplify movements associated with non-periodic and transient events. Also, the motion amplification does not have to be "played back" in the traditional video sense or in the form of a movie file per se. It can be used in an interactive piece of software enabling the user to can go backwards and forwards from frame to frame in any manner desired. One example would be to have a slider on the GUI, with which the user, by moving it back and forth, would control what frame is displayed.

Example

Thresholds and limits may be set for the entire differenced image or certain regions for a computer system to autonomously make decisions without human interaction. If certain pixels or groups of pixels behave in certain way then action by the computer can be taken without human interaction. An example of this may be intensity level changes indicative of motion in a certain direction, motion above a certain threshold, or motion of specific components being present. These are a few examples of a multitude of events triggering a reaction. Events could trigger a reaction or action in correlation to an outside event that is inputted into the system from an outside source.

The information gathered from this system could be used to control outside systems, for example, a feedback response control, alarming system, or process control. A multitude of outside systems could be integrated with the system.

Application to Process Control

As noted earlier, various components may exhibit motions even though they are intended to be substantially stationary. For example, pipes and ducts may vibrate or move aperiodically in response to something changing inside (pressure, density, temperature, fluid cavitation, "water hammer", etc.). Vibrations may be characteristic of other changes, such as the buildup of coke in refinery equipment, clogging or bridging in cement kilns, or sudden changes in the feed material in a mill or classifier. Applicants contemplate that the invention could be applied to such problems in cases where experimentation can definitively calibrate particular external movements with particular internal process attributes.

Application to Quality Control

Applicants have found that the invention is able to detect variations over time from motion across a contrast change with a high level of precision. In some cases this is sub-pixel motion. In the case where unwanted defects or non-uniformities exist, Applicants have discovered that the system may be used to detect those regions as described in the following Examples.

Example

An object might have a small flaw in the surface that is very difficult to see by simple visual inspection. To enhance the detection of this flaw, the object may be vibrated at a particular frequency while a camera views its surface. That frequency would preferably be a known frequency selected to be easily detected by the camera operating at a known frame rate. The system would then highlight motions related to that frequency, i.e., the image of the flaw moving back and forth at the vibrating frequency imposed on the object. The result would be any region in the scene with a contrast change would be detected when the object is vibrated. Areas of high uniformity would go otherwise unnoticed by the system. Thresholds may be set to determine whether or not a detected signal is considered a positive detection.

Example

A painted object that is supposed to have a highly uniform finish would be particularly suited for this type of inspection. For example, in auto manufacturing, exterior components such as doors, must be inspected for irregularities in the paint job. An inspection system could bring the door in front of the camera. The door would then be vibrated at a convenient frequency, e.g., 10 Hz. The system then isolates the 10 Hz motion. The system analyzes the 10 Hz image looking for regions in which a detection of modulated signal exists. If the detection occurs and it is above a certain threshold the system identifies a defect.

It will be appreciated that such an inspection process is inherently faster, more accurate, and more consistent than human visual inspection.

Application to Alignment

Aligning a shaft or other piece of equipment is a critical process that is needed from time to time or on initial installation of equipment. The alignment is necessary for properly maintaining function of equipment. A misaligned shaft can cause unnecessary wear, improper production of product and reduce equipment life. The inventive methods can be used to properly align equipment. A camera can be placed on one side of the alignment location, perhaps on one side of a coupling. The camera may look at an existing edge or perhaps a calibrated edge placed by a user. The camera can then monitor that edge and make displacement reading on the edge to determine positional changes over various operating conditions. That information can then be used to determine the proper alignment positions. In another instance a second camera may be placed on the opposite side of the alignment location so two camera look at either side of the alignment location.

The cameras may be positioned so they can rotate with the shaft to measure different orientations. In another instance one or more cameras may be placed away from and not on the equipment to measure the displacement of the shaft from a distance in one or more directions.

Alternatively, a camera may be place on one side of the shaft. The camera may track the position of the shaft at one location in space as the shaft rotates. This would effectively measure the shaft orbit and describe the current alignment of the shaft. These values can be used to align the shaft.

This can all be done while equipment is in operation or off. This would allow for operational situations such as thermal expansion to be considered.

I claim:
1. A method for monitoring an object, comprising:
acquiring a video file of the object as a sequence of video images comprising individual image frames, wherein each image frame is divided into pixels defined by spatial coordinates within the frame, and wherein brightness within each pixel is characterized with numerical values;
selecting at least two image frames acquired at different times and containing the object, a first such image frame being designated as a reference frame and at least one other image frame being designated as a differenced frame;
comparing the reference frame to the differenced frame by determining a variation in brightness based on differences in numerical values between at least one corresponding pixel having the same spatial coordinates in each of the two image frames, in which the variation indicates movement of the object;
amplifying the differences in numerical values between the two image frames by multiplying the difference by a predetermined factor to at least one amplified differenced frame;
creating at least one new image frame by superimposing the at least one amplified differenced frame onto the reference frame; and
displaying the at least one new image frame.
2. The method of claim 1, further comprising setting a frame rate for acquiring the video file by adjusting a temporal length of each image frame based on a frequency of periodic vibrations.
3. The method of claim 2, wherein a plurality of image frames are displayed as a sequence of new image video frames.
4. The method of claim 1, wherein determining a variation in brightness based on differences in numerical values comprises comparing a plurality of pixels from at least three image frames acquired at different times, in which each compared image frame is spaced a selected number of frames from another compared image frame.
5. The method of claim 4, further comprising determining a pixel undergoing the greatest change among the compared image frames by calculating a sum of differences in numerical values for each of the plurality of pixels within the compared image frames.
6. A system for monitoring an object, comprising:
a device that acquires video image files comprising a sequence of video images, each video image comprising an individual image frame;
a memory for storing the video image files and a processor executing computer-readable program instructions configured to identify pixels in an image frame, which are defined by spatial coordinates within the frame;
wherein brightness within each pixel is characterized with numerical values such that at least one pixel in a first image frame is capable of being compared to a corresponding pixel in a second image frame having the same spatial coordinates;

the system being further configured:

to compare the first and second image frames and determine a variation in brightness based on differences in numerical values between the at least one pixel in the first image frame and the corresponding pixel or pixels in the second image frame, in which the variation indicates movement of the object;

to amplify the differences in numerical values between the two image frames by multiplying the difference by a predetermined factor to at least one amplified differenced frame;

to create at least one new image frame by superimposing the at least one amplified differenced frame onto the reference frame; and and to provide to a user interface an output of the at least one new image frame.

7. The system of claim 6, wherein the device for acquiring video files is selected from the group consisting of: video cameras, infrared imagers, webcams, and digital cameras integral in a mobile device.

8. The system of claim 6, wherein the system is further configured to display a plurality of image frames as a sequence of new image video frames.

9. The system of claim 6, wherein the system is further configured to determine a variation in brightness based on differences in numerical values by comparing a plurality of pixels from at least three image frames acquired at different times, in which each compared image frame is spaced a selected number of frames from another compared image frame.

10. The system of claim 9, wherein the system is further configured to determine a pixel undergoing the greatest change among the compared image frames, by calculating a sum of differences in numerical values for each of the plurality of pixels within the compared image frames.

* * * * *